(12) United States Patent
Watson et al.

(10) Patent No.: US 6,235,754 B1
(45) Date of Patent: May 22, 2001

(54) METHODS AND COMPOSITIONS FOR PROTECTING ANIMALS AND HUMANS AGAINST ATTACK AND INFESTATION BY ARTHROPOD AND HELMINTH PARASITES

(75) Inventors: David Wesley Watson, Apex, NC (US); Kathleen Heaney; Kurt Schwinghammer, both of Yardley, PA (US)

(73) Assignee: American Cyanamid Company, Madison, NJ (US)

( * ) Notice: Subject to any disclaimer, the term of this patent is extended or adjusted under 35 U.S.C. 154(b) by 0 days.

(21) Appl. No.: 09/235,932

(22) Filed: Jan. 22, 1999

Related U.S. Application Data

(60) Provisional application No. 60/073,097, filed on Jan. 30, 1998.

(51) Int. Cl.[7] .................................................. A61K 31/445
(52) U.S. Cl. ............................................................. 514/315
(58) Field of Search ................................................ 514/315

(56) References Cited

U.S. PATENT DOCUMENTS 5,248,834    9/1993   Elliott et al. .......................... 528/638

FOREIGN PATENT DOCUMENTS

| 0811593 | * 12/1997 | (EP) . |
| 2288803 | 11/1995 | (GB) . |
| WO 94/06741 | 3/1994 | (WO) . |
| WO 97/16067 | 5/1997 | (WO) . |

\* cited by examiner

Primary Examiner—Kevin E. Weddington
(74) Attorney, Agent, or Firm—Joseph M. Mazzarese

(57) ABSTRACT

The present invention relates to methods and compositions for treating animals and humans, and for controlling, preventing and protecting animals and humans from infestation and infection by arthropod and helminth parasites by administering or applying to the animals, humans or their environment a 1,4-diaryl-2-fluoro-2-butene or 1,4-diaryl-2,3-difluoro-2-butene compound having the structural formula

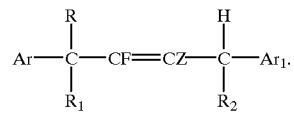

(I)

25 Claims, No Drawings

METHODS AND COMPOSITIONS FOR PROTECTING ANIMALS AND HUMANS AGAINST ATTACK AND INFESTATION BY ARTHROPOD AND HELMINTH PARASITES

This application claims benefit of Provisional No. 60/073,097, filed Jan. 30, 1998.

BACKGROUND OF THE INVENTION

Arthropod and helminth parasites cause hundreds of millions of dollars in economic damage annually on a global basis. In particular, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals.

In spite of the commercial parasiticides available today, damage to humans, livestock and companion animals still occurs. Accordingly, there is ongoing research to create new and more effective parasiticides.

It is, therefore, an object of the present invention to provide a method for treating animals and humans, and for controlling, preventing and protecting animals and humans from infestation and infection by arthropod and helminth parasites.

It is also an object of the present invention to provide a composition for treating animals and humans, and for controlling, preventing and protecting animals and humans from infestation and infection by arthropod and helminth parasites.

These and other objects of the present invention will become more apparent from the detailed description thereof set forth below.

SUMMARY OF THE INVENTION

The present invention provides a method of treatment for controlling, preventing and protecting animals and humans from infestation and infection by arthropod and helminth parasites which comprises administering or applying to the animals, humans or their environment a parasiticidally effective amount of a 1,4-diaryl-2-fluoro-2-butene or 1,4-diaryl-2,3-difluoro-2-butene compound having the structural formula I

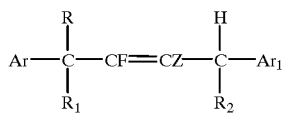

(I)

wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl, or R and $R_1$ taken together with the carbon atom to which they are attached form a $C_3$–$C_6$cycloalkyl ring optionally substituted with any combination of from one to three halogen or $C_1$–$C_4$alkyl groups, provided that when Z is F, $R_1$ is hydrogen;

Z is hydrogen or F;

$R_2$ is hydrogen, Cl, Br, cyano or $OR_3$;

$R_3$ is hydrogen or $C_1$–$C_4$alkyl; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$—$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and the optical isomers thereof, and the (E)- and (Z)-isomers thereof.

This invention also provides compositions for treating animals and humans, and controlling, preventing and protecting animals and humans from infestation and infection by arthropod and helminth parasites. The compositions of the present invention comprise an agronomically or pharmaceutically acceptable carrier and an arthropod or helminth parasiticidally effective amount of a formula I compound. Advantageously, it has been found that the 1,4-diaryl-2-fluoro-2-butene and 1,4-diaryl-2,3-difluoro-2-butene compounds of this invention, and compositions containing them, are especially useful in the practice of the invention against infestation and infection by flies, fleas, lice, mosquitoes, gnats, mites and ticks.

DETAILED DESCRIPTION OF THE INVENTION

The 1,4-diaryl-2-fluoro-2-butene and 1,4-diaryl-2,3-difluoro-2-butene compounds which are useful in the methods and compositions of this invention have the structural formula I

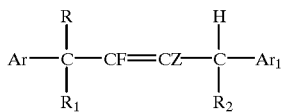

wherein R, $R_1$, $R_2$, Z, Ar and $Ar_1$ are as described hereinabove for formula I.

Preferred formula I compounds for use in the methods and compositions of this invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl provided that at least one of R and $R_1$ is other than hydrogen, or R and $R_1$ taken together with the carbon atom to which they are attached form a $C_3$–$C_6$cycloalkyl ring optionally substituted with any combination of from one to three halogen or $C_1$–$C_4$alkyl groups, provided that when Z is F, $R_1$ is hydrogen;

Z is hydrogen or F;

$R_2$ is hydrogen, Cl, Br, cyano or $OR_3$;

$R_3$ is hydrogen or $C_1$–$C_4$alkyl; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

More preferred formula I compounds are those wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl and $R_1$ is hydrogen, or R and $R_1$ are methyl, or R and $R_1$ taken together with the carbon atom to which they are attached form a cyclopropyl ring, provided that when Z is F, $R_1$ is hydrogen;

Z is hydrogen or F;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Another group of more preferred formula I compounds for use in the present invention are 1,4-diaryl-2-fluoro-2-butene compounds wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl and $R_1$ is hydrogen, or R and $R_1$ are methyl, or R and $R_1$ taken together with the carbon atom to which they are attached form a cyclopropyl ring;

Z is hydrogen;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

1,4-Diaryl-2-fluoro-2-butene compounds which are especially useful in the methods and compositions of this invention are those wherein Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl;

$R_1$ is hydrogen;

Z is hydrogen;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

Formula I compounds which are particularly useful in the practice of this invention against infestation and infection by arthropod parasites include 4-(p-chlorophenyl)-3-fluoro-1-(4-fluoro-3-phenoxyphenyl)-4-methyl-2-pentene, (Z)-;

1-[1-(p-chlorophenyl)-2-fluoro-4-(4-fluoro-3-phenoxyphenyl)-2-butenyl]cyclopropane, (Z)-;

1-[1-(p-chlorophenyl)-2-fluoro-4-(m-phenoxyphenyl)-2-butenyl]cyclopropane, (Z)-;

4-(p-ethoxyphenyl)-3-fluoro-1-(4-fluoro-3-phenoxyphenyl)-5-methyl-2-hexene, (Z)-;

1-[1-(p-ethoxyphenyl)-2-fluoro-4-(4-fluoro-3-phenoxyphenyl)-2-butenyl]cyclopropane, (Z)-;

4-(p-ethoxyphenyl)-3-fluoro-5-methyl-1-(m-phenoxyphenyl)-2-hexene, (Z)-;

1-{1-(p-chlorophenyl)-2-fluoro-4-[m-(p-fluorophenoxy)phenyl]-2-butenyl}cyclopropane, (Z)-;

1-[1-(p-ethoxyphenyl)-2-fluoro-4-(m-phenoxyphenyl)-2-butenyl]cyclopropane, (R,S)-(Z)-;

1-[2-fluoro-1-(p-fluorophenyl)-4-(m-phenoxyphenyl)-2-butenyl]cyclopropane, (R,S)-(Z)-;

1-{1-(p-ethoxyphenyl)-2-fluoro-4-[4-fluoro-3-(p-fluorophenoxy)phenyl]-2-butenyl}cyclopropane, (R,S)-(Z)-;

2,3-difluoro-1-(4-fluoro-3-phenoxyphenyl)-5-methyl-4-[p-(trifluoromethoxy)phenyl]-2-hexene, (E)-; and 1-{[1-(p-chlorophenyl)-2-fluoro-4-[4-fluoro-3-(p-fluorophenoxy)phenyl]-2-butenyl]}cyclopropane, (R,S)-(Z)-, among others.

The methods and compositions of the present invention are useful for controlling, preventing and protecting animals and humans from infestation and infection by arthropod parasites including, but not limited to, fleas, ticks, lice, mosquitoes, gnats, flies, biting flies, warble flies, muscoid flies, sheep ked, myiasitic fly larvae including those causing enteric myiasis and nasal bot, mites, chiggers and other biting, sucking and burrowing parasites of animals including, but not limited to, cattle, sheep, horses, deer, camels, swine, goats, ferrets, mink, rabbits, amphibians, reptiles, fish, birds, poultry, dogs and cats and humans. The methods and compositions of this invention are especially useful against flies, fleas, lice, mosquitoes, gnats, mites and ticks.

The 1,4-diaryl-2-fluoro-2-butene and 1,4-diaryl-2,3-difluoro-2-butene compounds are effective against arthropod parasites of animals and humans from the Subclass Acari, including members of Orders Mesostigmata (e.g., fowl mites), Acariformes, including suborders Prostigmata (e.g., demodectic mites), Astigmata (e.g., psoroptic and sarcoptic mites) and Cryptostigmata (e.g., beetle mites) and Acarina, including members of Families Ixodoidea, Ixodidae (e.g., hard ticks) and Argasidae (e.g., soft ticks). The compounds are also effective against arthropod parasites of animals and humans of the Class Insecta, including members of the Orders Diptera (Simuliidae, Phlebotominae, Ceratopogonidae, Culcidae, Rhagionidae, Athericidae, Chloropidae, Sarcophagidae, Tabanidae, Muscidae, Hippoboscidae and Calliphoridae), Siphonaptera (including fleas of the genera Ctenocephalides, Echidnophaga, Pulex, and Xenopsylla), Malloghaga (including biting lice of the genera Bovicola, Trichodectes and Damilina), Anoplura (including sucking lice of the genera Haematopinus, Linognathus and Solenopotes) and Hemiptera. The compounds are useful during all life stages of the above mentioned parasites.

The methods and compositions of the present invention are also useful for controlling, preventing and protecting animals and humans from infestation and infection by helminth parasites from the class Trematoda including members of the order Digenea (e.g., *Fasciola hepatica*); the class Cotyloda (e.g., Diphyllobothrium spp. and Spirometra spp.); the class Eucestoda (e.g., Moniezia spp., Talnia spp. and Echinococcus spp.); and the class Nematoda including members of the orders Rhabditida, Strongylida (e.g., Haemonchus spp., Ostertagia spp., Cooperia spp. and Ancyclostoma spp.), Oxyurida (e.g., Oxyuris spp.), Ascaridida (e.g., Toxacara spp.), Spirurida (e.g., Dracunculus spp., Thelazia spp., Onchocera spp. and Dirofilaria spp.), and Enoplida (e.g., Trichuris spp.). The formula I compounds of this invention are useful during all life stages of the above mentioned parasites.

Advantageously, it has been found that the formula I compounds are effective against populations of the parasites mentioned above which exhibit resistance to other parasiticidal compounds, such as synthetic pyrethroids. In addition, the compounds may be used in combination or conjunction with one or more other parasiticidal compounds including, but not limited to, anthelmintics, such as benzimidazoles, piperazine, levamisole, pyrantel, praziquantel and the like; endectocides such as avermectins, milbemycins and the like; ectoparasiticides such as arylpyrroles including chlorfenapyr, organophosphates, carbamates, gamabutyric acid inhibitors including fipronil, pyrethroids, spinosads, imidacloprid and the like; insect growth regulators such as pyriproxyfen, cyromazine and the like; and chitin synthase inhibitors such as benzoylureas including flufenoxuron.

The formula I compounds may also be used in combination or conjunction with one or more conventional synergists such as piperonyl butoxide, N-octyl bicycloheptene dicarboximide, dipropyl pyridine-2,5-dicarboxylate and 1,5a,6,9,9a,9b-hexahydro-4a(4H)-dibenzofurancarboxaldehyde to enhance efficacy, broaden spectrum and provide a convenient method for parasite control.

The formula I compounds may be applied topically to the skin, hide, fur, feathers or hair of the animal or human as a pour-on, spot-on, spray, dip, back-rubber, wettable powder, dust, emulsifiable concentrate, aqueous flowable, shampoo, paste, foam, cream, solution, suspension or gel. Those compositions generally contain about 0.1 ppm to 700,000 ppm of the active compound. In addition, the compound may be presented in the form of a solid matrix such as an ear tag, collar or medallion.

The formula I compounds may also be administered orally, intragastrically or intrarumenally as a solution, paste, gel, tablet, bolus or drench or mixed in feed when prepared as a feed premix. Such administration is particularly useful for the control of enteric and somatic myiasis and to prevent development of the parasite in the feces and urine of treated animals and humans. In addition, the formula I compounds may be parenterally administered to the animals and humans.

The formula I compounds may also be applied to the environment in which the animals or humans inhabit as a spray, powder, bait, solid matrix, solution, wettable powder, emulsifiable concentrate or fumigant. These environments may include, but are not limited to, homes, yards, barns, pens, kennels, poultry houses, feed lots, stables, stalls, offices, workplaces, food preparation facilities, dairies, fisheries, aviaries, zoos and the like.

The amount of active compound which is administered or applied to the animals, humans or their environment will vary depending upon the particular compound, target pest (s), application or administration method, and the particular host to be treated. Those skilled in the art can readily determine what a pesticidally effective amount is without undue experimentation.

In formula I above, 5- and 6-membered heteroaromatic rings include, but are not limited to, pyridyl, pyrazolyl, imidazolyl, triazolyl, isoxazolyl, tetrazolyl, pyrazinyl, pyridazinyl, triazinyl, furanyl, thienyl and thiazolyl rings each optionally substituted as described in formula I above.

Exemplary of halogen hereinabove are fluorine, chlorine, bromine and iodine. The terms "$C_1$–$C_4$haloalkyl", "$C_3$–$C_6$halocycloalkyl" and "$C_1$–$C_4$haloalkoxy" are defined as a $C_1$–$C_4$alkyl group, a $C_3$–$C_6$cycloalkyl group and a $C_1$–$C_4$alkoxy group substituted with one or more halogen atoms, respectively.

In a preferred embodiment of the present invention, the fluorine atom and the Z group attached to the carbon atoms of the double bond in the formula I compounds are in the (E)- configuration with respect to each other.

Flow Diagram I illustrates a method for preparing 1,4-diaryl-2-fluoro-2-butene compounds wherein R and R are each independently $C_1$–$C_4$alkyl, $C_1$–$C_4$haloalkyl, $C_3$–$C_6$cycloalkyl or $C_3$–$C_6$halocycloalkyl, or R and $R_1$ taken together with the carbon atom to which they are attached form a $C_3$–$C_6$cycloalkyl ring optionally substituted with any combination of from one to three halogen or $C_1$–$C_4$alkyl groups; Z and $R_2$ are hydrogen; and the double bond is in the (Z)- configuration. This method comprises: reacting an arylacetonitrile of formula II with a selective reducing agent, such as diisobutylaluminum hydride, and quenching with water to form a 2-arylacetaldehyde of formula III; reacting the formula III compound with a zinc/triphenyl phosphine/carbon tetrabromide mixture to form a 3-aryl-1,1-dibromo-1-propene of formula IV; reacting the formula IV compound with a base such as an alkyllithium and phenyl cyanate to form a 4-aryl-2-butynenitrile of formula V; reacting the formula V compound with cesium fluoride, potassium hydrogen fluoride and water in N,N-dimethylformamide to form a 4-aryl-3-fluoro-2-butenenitrile, (Z)- of formula VI; selectively reducing the formula VI compound with a reducing agent such as diisobutylaluminum hydride and quenching with water to form a 4-aryl-3-fluoro-2-butenal, (Z)- of formula VII; reducing the formula VII compound with a conventional reducing agent such as lithium aluminum hydride or sodium borohydride to form a 4-aryl-3-fluoro-2- buten-1-ol, (Z)- of formula VIII; reacting the formula VIII compound with a brominating agent, such as a triphenyl phosphine and bromine mixture, in the presence of a solvent, such as a halogenated hydrocarbon, to form a 4-aryl-1-bromo-3-fluoro-2-butene, (Z)- of formula IX; and reacting the formula IX compound with about 0.0025 to 0.1 molar equivalent of a palladium catalyst, such as bis(dibenzylideneacetone)palladium(0) (Pd(dba)$_2$), bis(acetonitrile)palladium(II) chloride, bis(triphenylphosphine)palladium(II) chloride, tetrakis(triphenylphosphine)palladium(0) and the like, at least about 2 molar equivalents of a base, such as an alkali metal carbonate, an alkaline earth metal carbonate, an alkali metal hydrogen carbonate, an alkali metal hydroxide, an alkaline earth metal hydroxide, an alkali metal $C_1$–$C_6$alkoxide and the like, and a boronic acid of formula X in the presence of a solvent, such as an aromatic hydrocarbon, a halogenated aromatic hydrocarbon, a $C_1$–$C_4$alcohol, and the like, and mixtures thereof.

intermediate compounds described hereinabove which are predominantly in the (Z)- configuration using conventional procedures such as exposure to light.

Formula I compounds wherein $R_1$, $R_2$ and Z are hydrogen may be prepared, as indicated in Flow Diagram II, by reacting a ketone or aldehyde of formula XI with an ester of formula XII in the presence of a base such as sodium hydride or lithium diisopropylamide to form a 3-aryl-2-fluoro-2-propenate of formula XIII, reducing the formula XIII compound with a reducing agent such as lithium aluminum hydride to form a 3-aryl-2-fluoro-2-propen-1-ol of formula XIV, oxidizing the formula XIV compound with an oxidizing agent such as manganese(IV) oxide to form a 3-aryl-2-fluoro-2-propenal of formula XV, reacting the formula XV compound with an ylide of formula XVI in the presence of a base such as sodium hydride, an alkyllithium or lithium diisopropylamide to form a diene of formula XVII, and reacting the formula XVII compound with magnesium in the presence of a protic solvent such as a $C_1$–$C_4$alcohol.

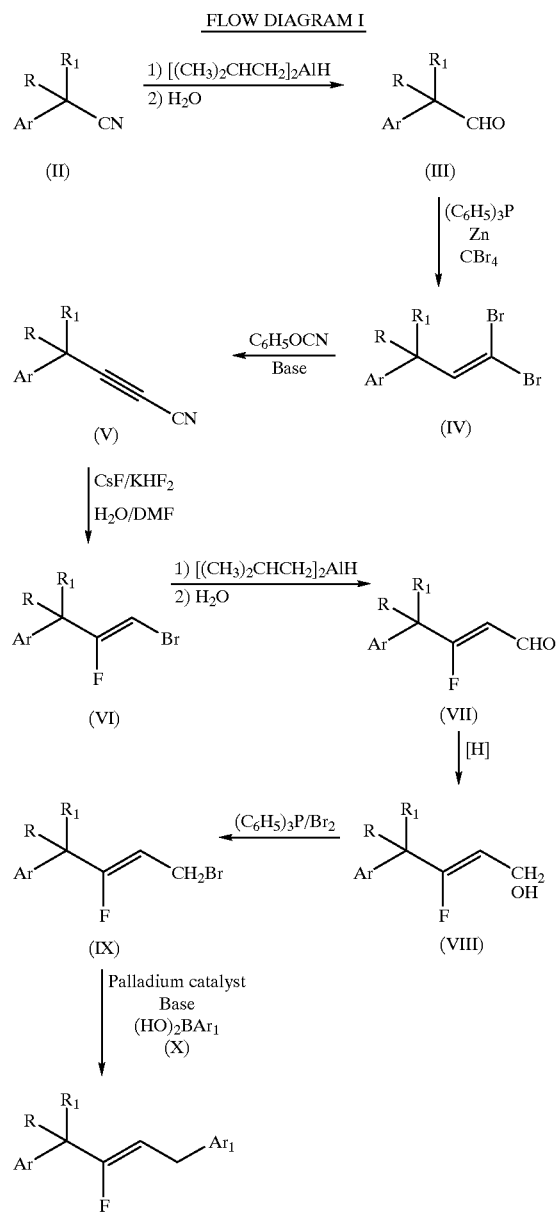

FLOW DIAGRAM I

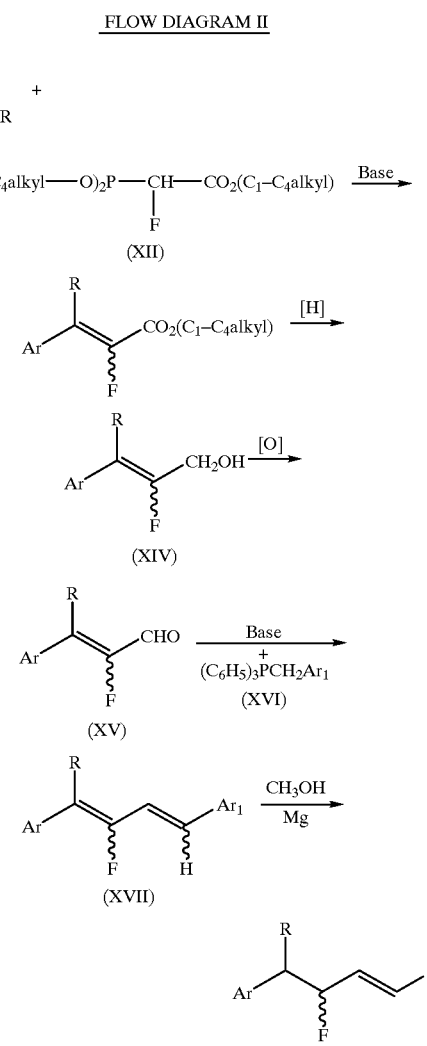

FLOW DIAGRAM II

Formula I compounds wherein the double bond is in the (E)- configuration may be prepared by isomerizing certain Alternatively, formula XVII diene compounds may be prepared, as indicated in Flow Diagram III, by reacting a 3-aryl-2-fluoro-2-propen-1-ol of formula XIV with thionyl chloride in the presence of a solvent such as pyridine to form a 3-aryl-1-chloro-2-fluoro-2-propene of formula XVIII, reacting the formula XVIII compound with triphenylphosphine to form an ylide of formula XIX, and reacting the formula XIX compound with a base such as sodium hydride and an aldehyde of formula XX.

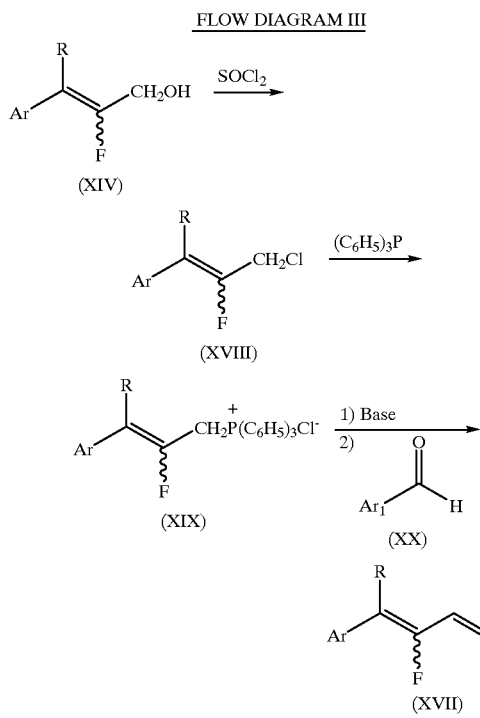

FLOW DIAGRAM III (XIV)

(XVIII)

(XIX) + (XX)

(XVII)

Advantageously, intermediate 3-aryl-2-fluoro-2-propenal compounds of formula XV may be prepared, as illustrated in Flow Diagram IV, by reacting an aldehyde or ketone of formula XI with an alkoxymethyl triphenyl phosphonium halide of formula XXI in the presence of a base such as butyllithium to form a 2-arylvinyl methyl ether of formula XXII, reacting the formula XXII compound with dichlorofluoromethane and a base such as potassium hydroxide in the presence of water and optionally a phase transfer catalyst such as 18-crown-6 to form an intermediate, and reacting the intermediate in situ with water at an elevated temperature, preferably about 60 to 90° C.

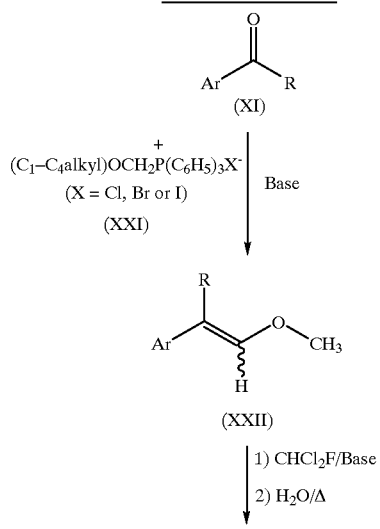

FLOW DIAGRAM IV (XI)

+ $(C_1-C_4 alkyl)OCH_2P(C_6H_5)_3X^-$
(X = Cl, Br or I)
(XXI)

Base (XXII)

1) $CHCl_2F$/Base
2) $H_2O/\Delta$

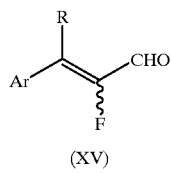

(XV)

1,4-Diaryl-2,3-difluoro-2-butene compounds wherein $R_1$ is hydrogen and Z is F may be prepared, as illustrated in Flow Diagram V, by reacting a 3-aryl-1,1,2-trifluoro-1-propene compound of formula XXIII with sodium bis(2-methoxyethoxy)aluminum hydride and a mineral acid such as hydrochloric acid to form a 3-aryl-1,2-difluoro-1-propene compound of formula XXIV, and sequentially reacting the formula XXIV compound with an alkyllithium such as n-butyllithium, zinc chloride, tetrakis(triphenylphosphine)palladium(0) and a substituted methyl halide of formula XXV.

FLOW DIAGRAM V

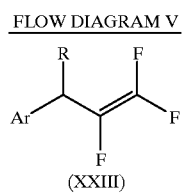

(XXIII)

1) $[(CH_3OCH_2CH_2O)_2AlH_2]Na$
2) $H^+$

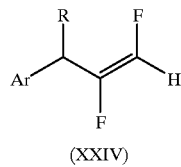

(XXIV)

1) $CH_3(CH_2)_3Li$
2) $ZnCl_2$
3) $Pd[P(C_6H_5)_3]_4$
4) $XCH_2Ar_1$
   (XXV)
   (X = Cl, Br or I)

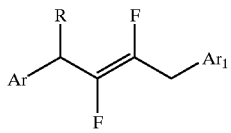

Formula I compounds wherein Z is F and $R_2$ is hydroxy may be prepared, as shown in Flow Diagram VI, by reacting a 3-aryl-1,2-difluoro-1-propene compound of formula XXIV with an alkyllithium such as n-butyllithium and an aldehyde of formula XXVI.

FLOW DIAGRAM VI

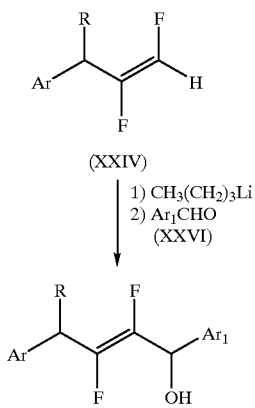

(XXIV)

1) $CH_3(CH_2)_3Li$
2) $Ar_1CHO$
   (XXVI)

Formula I compounds wherein the fluorine atoms about the double bond are in the (Z)- configuration may be prepared by isomerizing the formula XXIV compounds described hereinabove which are predominately in the (E)- configuration using conventional procedures such as exposure to light.

Compounds of formula I wherein $R_2$ is Cl or Br may be prepared by reacting a formula I compound wherein $R_2$ is hydroxy with thionyl chloride or thionyl bromide. The reaction scheme is shown below in Flow Diagram VII.

FLOW DIAGRAM VII

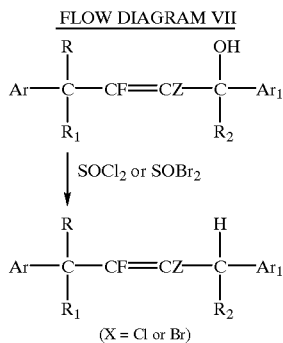

$SOCl_2$ or $SOBr_2$ (X = Cl or Br)

Alternatively, formula I compounds wherein $R_2$ is Cl or Br may be prepared by halogenating a formula I compound wherein $R_2$ is hydrogen with a chlorinating agent such as N-chlorosuccinimide or a brominating agent such as N-bromosuccinimide. The reaction scheme is shown below in Flow Diagram VIII.

FLOW DIAGRAM VIII

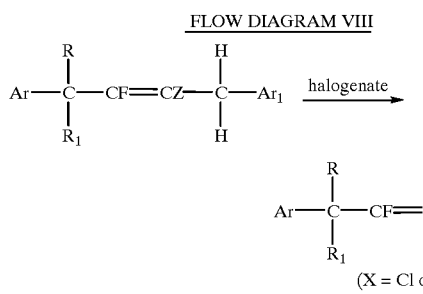

halogenate (X = Cl or Br)

Formula I compounds wherein $R_2$ is cyano may be prepared by reacting a formula I compound wherein $R_2$ is Cl or Br with sodium cyanide. The reaction scheme is shown in Flow Diagram IX.

FLOW DIAGRAM IX

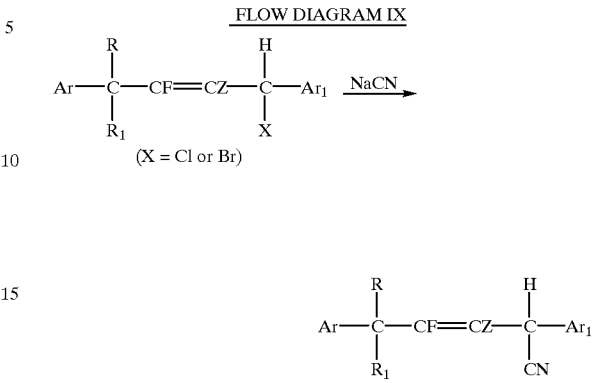

(X = Cl or Br)

NaCN

Alternatively, formula I compounds wherein $R_2$ is cyano may be prepared, as illustrated in Flow Diagram X, by reacting a formula I compound wherein $R_2$ is hydroxy with methanesulfonyl chloride (mesyl chloride) or p-toluenesulfonyl chloride (tosyl chloride) in the presence of a base to form an intermediate compound of formula XXVII, and reacting the intermediate compound with sodium cyanide.

FLOW DIAGRAM X

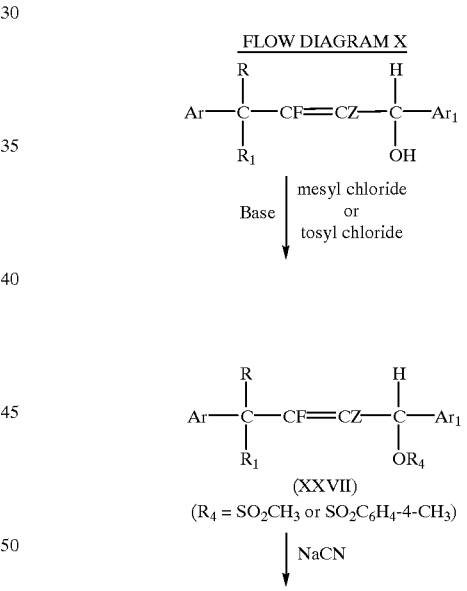

Base | mesyl chloride or tosyl chloride (XXVII)
($R_4 = SO_2CH_3$ or $SO_2C_6H_4$-4-$CH_3$)

NaCN

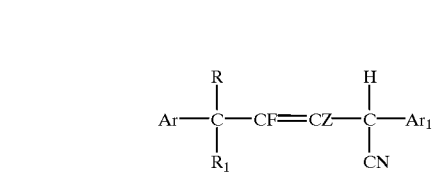

Formula I compounds wherein $R_2$ is $OR_3$ may be prepared as shown below in Flow Diagram XI.

FLOW DIAGRAM XI

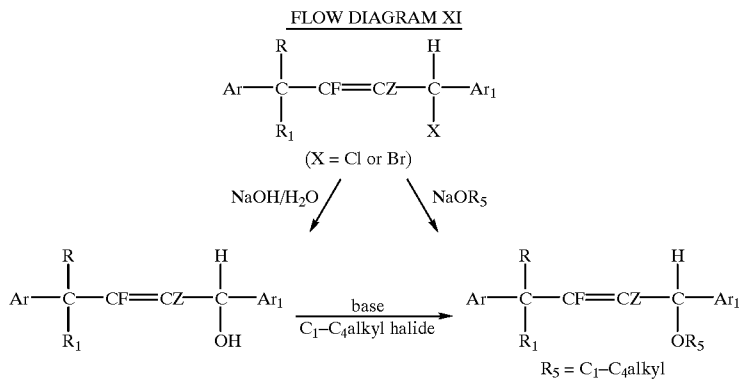

(X = Cl or Br)

$R_5 = C_1–C_4 \text{alkyl}$

Starting formula XXIII compounds may be prepared, as shown in Flow Diagram XII, by sequentially reacting bromotrifluoroethylene with zinc, copper(I) bromide and a substituted methyl bromide of formula XXVIII or a trifluoroacetate of formula XXIX.

FLOW DIAGRAM XII

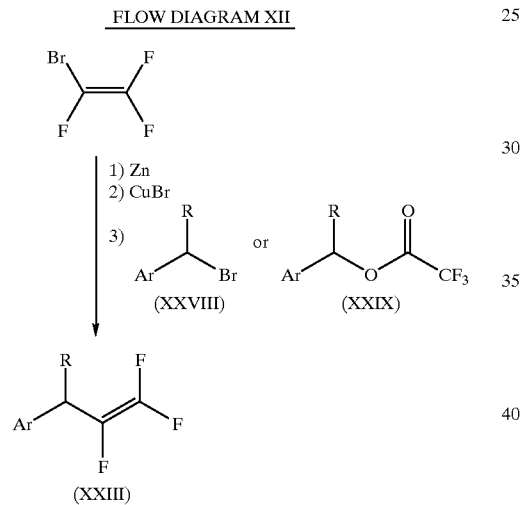

Intermediate compounds of formula XXVIII may be prepared, as illustrated in Flow Diagram XIII, by reacting an arylmagnesium bromide compound of formula XXX with an aldehyde of formula XXXI and a mineral acid to form an alcohol of formula XXXII, and reacting the formula XXXII alcohol with hydrobromic acid.

FLOW DIAGRAM XIII

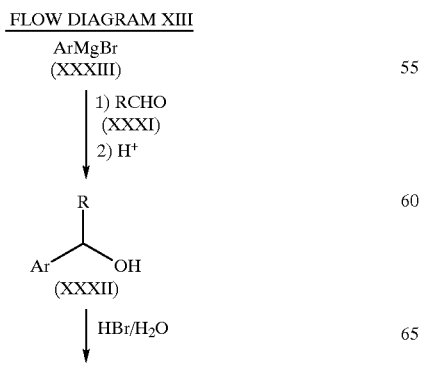

-continued

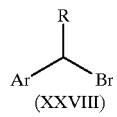

(XXVIII)

Compounds of formula XXIX may be prepared by reacting a formula XXXII alcohol with trifluoroacetic anhydride. The reaction scheme is shown in Flow Diagram XIV.

FLOW DIAGRAM XIV

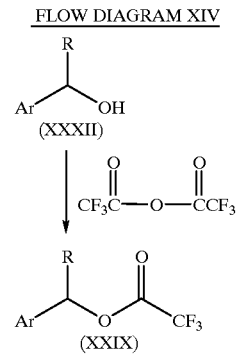

Intermediate alcohols of formula XXXII may also be prepared, as shown in Flow Diagram XV, by reacting an aryl bromide of formula XXXIII with an alkyllithium such as n-butyllithium and an aldehyde of formula XXXI.

FLOW DIAGRAM XV

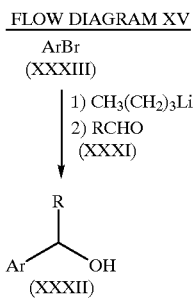

In order to facilitate a further understanding of the invention, the following examples are presented primarily for the purpose of illustrating more specific details thereof. The scope of the invention should not be deemed limited by the examples, but encompasses the entire subject matter defined in the claims.

EXAMPLE 1

Evaluation of Test Compounds Against the Adult Cat Flea, *Ctenocephalides felis*

This test is designed to evaluate the contact activity of test compounds against the adult cat flea. Test compounds are dissolved in 100% acetone to 300, 100, 10 and 1 ppm. 100 μL of each of these dilutions is added to the bottom of a 20 mL glass scintillation vial with a pipettor. The vial is allowed to dry under a fume hood for 15 minutes. The bottom of the vial measures 4.909 $cm^2$. The amount of test compound applied by each dilution equals 6.2, 2.0, 0.2 and 0.02 $\mu g/cm^2$, respectively. Newly emerged adult cat fleas are anesthetized with $CO_2$ to immobilize, and are counted into the scintillation vials with forceps. Five fleas are placed in each vial. These tests are done in replicates of two or three so that there are 10 to 15 fleas per rate/compound. Mortality readings are taken 4 and 24 hours after placing the fleas in the vials. Fleas which do not move when disturbed are considered dead. Percent mortality is then calculated for each treatment.

Data obtained are reported in Table I. Compounds employed in the evaluations of the present invention are given a compound number and identified by name. Data in Table I are reported by compound number.

| COMPOUNDS EVALUATED | |
|---|---|
| Compound Number | |
| 1 | 4-(p-Chlorophenyl)-3-fluoro-4-methyl-1-(m-phenoxyphenyl)-2-pentene, (Z)- and (E)- (95:5) |
| 2 | 4-(p-Chlorophenyl)-3-fluoro-1-(4-fluoro-3-phenoxyphenyl)-4-methyl-2-pentene, (Z)- |
| 3 | 1-(p-Chlorophenyl)-1-[1-fluoro-3-(m-phenoxyphenyl)propenyl]cyclopropane, (Z)- |
| 4 | 1-(p-Chlorophenyl)-1-[1-fluoro-3-(4-fluoro-3-phenoxyphenyl)propenyl]cyclopropane, (Z)- |
| 5 | 1-[1-(p-Chlorophenyl)-2-fluoro-4-(4-fluoro-3-phenoxyphenyl)-2-butenyl]cyclopropane, (Z)- |
| 6 | 1-[1-(p-Chlorophenyl)-2-fluoro-4-(m-phenoxyphenyl)-2-butenyl]cyclopropane, (Z)- |
| 7 | 4-(p-Chlorophenyl)-3-fluoro-1-(4-fluoro-3-phenoxyphenyl)-5-methyl-2-hexene, (Z)- |
| 8 | 4-(p-Chlorophenyl)-3-fluoro-5-methyl-1-(m-phenoxyphenyl)-2-hexene, (Z)- |
| 9 | 4-(p-Chlorophenyl)-3-fluoro-5-methyl-1-(m-phenoxyphenyl)-5-methyl-2-hexene, (Z)- |
| 10 | 1-[1-(p-Ethoxyphenyl)-2-fluoro-4-(4-fluoro-3-phenoxyphenyl)-2-butenyl]cyclopropane, (Z)- |
| 11 | 4-(p-Ethoxyphenyl)-3-fluoro-5-methyl-1-(m-phenoxyphenyl)-2-hexene, (Z)- |
| 12 | 4-(p-Ethoxyphenyl)-3-fluoro-1-[m-(p-fluorophenoxy)phenyl]-5-methyl-2-hexene, (Z)- |
| 13 | 1-{1-(p-Chlorophenyl)-2-fluoro-4-[m-(p-fluorophenoxy)phenyl]-2-butenyl}cyclopropane, (Z)- |
| 14 | 1-[1-(p-Ethoxyphenyl)-2-fluoro-4-(m-phenoxyphenyl)-2-butenyl]cyclopropane, (R,S)- (Z)- |
| 15 | 1-[2-Fluoro-1-(p-fluorophenyl)-4-(m-phenoxyphenyl)-2-butenyl]cyclopropane, (R,S)- (Z)- |
| 16 | 1-{1-(p-Ethoxyphenyl)-2-fluoro-4-[4-fluoro-3-(p-fluorophenoxy)phenyl]-2-butenyl}cyclopropane, (R,S)- (Z)- |
| 17 | 2,3-Difluoro-1-(4-fluoro-3-phenoxyphenyl)-5-methyl-4-[p-(trifluoromethoxy)phenyl]-2-hexene, (E)- |
| 18 | 1-{[1-(p-Chlorophenyl)-2-fluoro-4-[4-fluoro-3-(p-fluorophenoxy)phenyl]-2-butenyl}cyclopropane, (R,S)- (Z)- |

TABLE I

Evaluation of Test Compounds against *Ctenocephalides felis* (cat flea)

| Compound Number | Dose ($\mu g/cm^2$) | 4 Hour % Mortality | 24 Hour % Mortality |
|---|---|---|---|
| 1 | 6.20 | 0 | 53 |
|   | 2.00 | 10 | 35 |
|   | 0.20 | 5 | 20 |
|   | 0.02 | 5 | 10 |
| 2 | 6.20 | 22 | 100 |
|   | 2.00 | 0 | 58 |
|   | 0.20 | 0 | 32 |
|   | 0.02 | 5 | 10 |
| 3 | 6.20 | 0 | 13 |
|   | 2.00 | 7 | 17 |
|   | 0.20 | 0 | 7 |
|   | 0.02 | 5 | 5 |
| 4 | 6.20 | 3 | 28 |
|   | 2.00 | 0 | 21 |
|   | 0.20 | 7 | 14 |
|   | 0.02 | 5 | 16 |
| 5 | 6.20 | 98 | 100 |
|   | 2.00 | 79 | 100 |
|   | 0.20 | 39 | 81 |
|   | 0.02 | 34 | 69 |
| 6 | 6.20 | 80 | 100 |
|   | 2.00 | 56 | 88 |
|   | 0.20 | 0 | 28 |
|   | 0.02 | 0 | 8 |
| 7 | 6.20 | 0 | 100 |
|   | 2.00 | 0 | 0 |
|   | 0.20 | 0 | 0 |
|   | 0.02 | 0 | 10 |
| 8 | 6.20 | 0 | 20 |
|   | 2.00 | 0 | 0 |
|   | 0.20 | 0 | 0 |
|   | 0.02 | 0 | 10 |
| 9 | 6.20 | 20 | 80 |
|   | 2.00 | 30 | 70 |
|   | 0.20 | 0 | 70 |
|   | 0.02 | 0 | 40 |
| 10 | 6.20 | 100 | 100 |
|   | 2.00 | 70 | 100 |
|   | 0.20 | 68 | 95 |
|   | 0.02 | 10 | 20 |
| 11 | 6.20 | 60 | 90 |
|   | 2.00 | 30 | 90 |
|   | 0.20 | 10 | 40 |
|   | 0.02 | 0 | 10 |
| 12 | 6.20 | 33 | 78 |
|   | 2.00 | 10 | 30 |
|   | 0.20 | 0 | 10 |
|   | 0.02 | 0 | 0 |
| 13 | 6.20 | 10 | 95 |
|   | 2.00 | 5 | 67 |
|   | 0.20 | 0 | 33 |
|   | 0.02 | 0 | 5 |
| 14 | 6.20 | 50 | 100 |
|   | 2.00 | 20 | 100 |
|   | 0.20 | 20 | 60 |
|   | 0.02 | 10 | 30 |
| 15 | 6.20 | 100 | 100 |
|   | 2.00 | 80 | 100 |
|   | 0.20 | 44 | 78 |
| 16 | 6.20 | 100 | 100 |
|   | 2.00 | 71 | 100 |
|   | 0.20 | 20 | 50 |
|   | 0.02 | 0 | 60 |
| 17 | 6.20 | 10 | 90 |
|   | 2.00 | 10 | 50 |
|   | 0.20 | 10 | 40 |
|   | 0.02 | 0 | 20 |

EXAMPLE 2

Evaluation of Test Compounds Against the Larval American Dog Tick, *Dermacentor variabilis*

This test is designed to evaluate the contact activity of test compounds against the American dog tick. Test compounds are dissolved in 100% acetone to 1000, 300, 100, 10, 1 and 0.1 ppm. 100 μL of each of these dilutions is added to the bottom of a 20 mL glass scintillation vial with a pipettor. The vial is allowed to dry under a fume hood for 15 minutes. The vial is then turned in its side, and 250 μL of each dilution is applied to the sides of the vial. The vial is placed on a rolling machine and allowed to roll under the hood, coating the sides of the vial, until the acetone completely evaporates. The bottom of the vial measures 4.909 $cm^2$ and the sides measure 4.5 cm high×8.8 cm around, so that the total coated area of the scintillation vial measures 44.51 $cm^2$. The amount of test compound applied by each dilution equals 7.86, 2.36, 0.79, 0.079, 0.0079 and 0.00079 $\mu g/cm^2$, respectively. Unfed larval dog ticks are counted into the scintillation vials with a slightly damp paintbrush. Ten ticks are placed in each vial. These tests are done in replicates of two or three so that there are 20 to 30 ticks per rate/compound. Mortality readings are taken 4 and 24 hours after placing the ticks in the vials. To read the test, the vial is placed under a magnifying glass and tapped gently. Ticks which have a curled appearance and do not move when disturbed are considered dead. Percent mortality is then calculated for each treatment.

Data obtained are reported in Table II. The compounds evaluated are reported by compound number given in Example 1.

TABLE II

Evaluation of Test Compounds against *Dermacentor variabilis* (American dog tick)

| Compound Number | Dose ($\mu g/cm^2$) | 4 Hour % Mortality | 24 Hour % Mortality |
|---|---|---|---|
| 5 | 7.860 | 100 | 100 |
|   | 2.360 | 100 | 100 |
|   | 0.790 | 100 | 100 |
|   | 0.079 | 100 | 100 |
|   | 0.0079 | 100 | 100 |
|   | 0.00079 | 100 | 100 |
| 10 | 7.860 | 100 | 100 |
|   | 2.360 | 100 | 100 |
|   | 0.790 | 100 | 100 |
|   | 0.079 | 100 | 100 |

EXAMPLE 3

Evaluation of Test Compounds Against the Adult Horn Fly, *Haematobia irritans* (Pyrethroid-Susceptible and -Resistant)

This test is conducted using 9 cm Whatman No. 1 filter papers which are placed in 100×20 mm disposable plastic petri dishes. Test doses are expressed as μg of test substance per $cm^2$ of filter paper.

1) Prepare solutions of test compound in acetone such that 800 or 1000 μL contains the amount necessary to obtain the desired dose rate.
2) Pipette 800 or 1000 μL of test solution onto filter paper.
3) Filter papers are dried under a fume hood.
4) When dry, filter papers are placed in the petri dish tops. Dishes are generally held about 24 hours before test organism is added.
5) Two- to five-day-old horn flies (pyrethroid-susceptible or -resistant) which have had two or more blood meals are used in the assay. Flies are collected into a small vial from the holding cage. Vials are then chilled in a freezer for about 4 minutes to immobilize the flies. Immobilized flies are then distributed to petri dish bottoms, 12 to 25 flies per dish, then dishes are closed and inverted.
6) As soon as the flies become mobile (about 5 minutes), they are examined to detect any flies that are dead or injured. This number is subtracted from total number of flies in the dish.
7) Petri dishes are held at room temperature and examined at the desired time intervals which might be 10 minutes to 6 hours.
8) All dead flies are recorded at each examination time. A fly is considered dead if it cannot walk even though it may still be moving.
9) Each test has control dishes containing filter papers treated only with acetone.
10) Percent mortality at any time period is calculated using the following formula:

Number of dead flies−number dead @5 min/Total number of flies−number dead @5 min×100

Percent mortality is then corrected for control mortality using Abbot's formula.

Data for pyrethroid-susceptible horn flies are reported in Table III. Data for pyrethroid-resistant horn flies are reported in Table IV. The compounds evaluated are reported by compound number given in Example 1.

TABLE III

Evaluation of Test Compounds against adult, Pyrethroid-susceptible horn fly (*Haematobia irritans*)

| Compound Number | Dose ($\mu g/cm^2$) | 6 Hour % Mortality |
|---|---|---|
| 5 | 5.00 | 100 |
|   | 2.50 | 98 |
|   | 1.25 | 88 |
|   | 0.625 | 27 |
|   | 0.3125 | 5 |
|   | 0.1560 | 0 |
| 18 | 10.0 | 100 |
|   | 5.00 | 99 |
|   | 2.50 | 94 |
|   | 1.25 | 36 |
|   | 0.625 | 4 |
|   | 0.3125 | 1 |
|   | 0.1560 | 0 |

TABLE IV

Evaluation of Test Compounds against adult, Pyrethroid-resistant horn fly (*Haematobia irritans*)

| Compound Number | Dose ($\mu g/cm^2$) | 6 Hour % Mortality |
|---|---|---|
| 5 | 20.0 | 93 |
|   | 10.0 | 33 |
|   | 5.00 | 7 |
|   | 2.50 | 1 |
|   | 1.25 | 0 |
| 18 | 20.0 | 58 |
|   | 10.0 | 12 |

TABLE IV-continued

Evaluation of Test Compounds against adult, Pyrethroid-resistant horn fly (*Haematobia irritans*)

| Compound Number | Dose ($\mu g/cm^2$) | 6 Hour % Mortality |
|---|---|---|
| | 5.00 | 1 |
| | 2.50 | 0 |

EXAMPLE 4

Evaluation of Test Compounds Against the Adult House Fly, *Musca domestica*

This test is designed to evaluate the activity of test compounds against the house fly. Test compounds are dissolved in 100% acetone to 1000, 300, 100, 10 and 1 ppm. 100 μL of each of these dilutions is added to the bottom of a 20 mL glass scintillation vial with a pipettor. The vial is allowed to dry under a fume hood for 15 minutes. The vial is then turned on its side, and 250 μL of each dilution is applied to the sides of the vial. The vial is placed on a rolling machine and allowed to roll under the hood, coating the sides of the vial, until the acetone completely evaporates. The bottom of the vial measures 4.909 $cm^2$ and the sides measure 4.5 cm high×8.8 cm around, so that the total coated area of the scintillation vial measures 44.51 $cm^2$. The amount of test compound applied by each dilution equals 7.86, 2.36, 0.79, 0.079, and 0.0079 $\mu g/cm^2$, respectively. Included in all tests are two to three replications of untreated vials. Adult house flies which are five to seven days old are chilled in a freezer for five minutes to immobilize, and are placed on a sorting platform which provides a steady stream of $CO_2$ to keep the flies immobile. Five flies are counted into each scintillation vial with forceps. The top of the vial is plugged with a wad of sheet cotton sufficient to contain the flies. These tests are done in replicates of two to four so that there are 10 to 20 flies per rate/compound. Mortality readings are taken 1 and 4 hours after placing the flies in the vials. Flies which are unable to stand when disturbed are considered dead. Percent mortality is then calculated for each treatment.

Data obtained are reported in Table V. The compounds evaluated are reported by compound number given in Example 1.

TABLE V

Evaluation of Test Compounds against *Musca domestica* (house fly)

| Compound Number | Dose ($\mu g/cm^2$) | 1 Hour % Mortality | 4 Hour % Mortality |
|---|---|---|---|
| 10 | 2.360 | 40 | 100 |
| | 0.790 | 20 | 75 |
| | 0.079 | 20 | 60 |

EXAMPLE 5

Evaluation of Test Compounds Against the Adult Biting Louse, Bovicola spp.

This test is designed to evaluate the activity of test compounds against the biting louse. Test compounds are dissolved in 100% acetone to 300, 100 and 10 ppm. 100 μL of each of these dilutions is added to the bottom of a 20 mL glass scintillation vial with a pipettor. The vial is allowed to dry under a fume hood for 15 minutes. The bottom of the vial measures 4.909 $cm^2$. The amount of test compound applied by each dilution equals 6.1, 2.0 and 0.2 $\mu g/cm^2$, respectively. Included in all tests are two to three replications of untreated vials. Lice are collected from the host animal and are used within 4 hours. The lice are counted into the scintillation vials with a slightly damp paintbrush. Five adult lice are placed in each vial. These tests are done in replicates of two or three so that there are 10 to 15 lice per rate/compound. Mortality readings are taken at 2 and 4 hours after placing the lice in the vials. To read the test, the vial is placed under a magnifying glass. Lice which have a dried appearance and do not move when disturbed are considered dead. Percent mortality is then calculated for each treatment.

Data obtained are reported in Table VI. The compounds evaluated are reported by compound number given in Example 1.

TABLE VI

Evaluation of Test Compounds against *Bovicola spp.* (biting louse)

| Compound Number | Dose ($\mu g/cm^2$) | 2 Hour % Mortality | 4 Hour % Mortality |
|---|---|---|---|
| 5 | 6.1 | 100 | 100 |
| | 2.0 | 92 | 100 |

EXAMPLE 6

Evaluation of Compositions Containing Test Compounds and Piperonyl Butoxide Against the Adult Cat Flea, *Ctenocephalides felis*

This test evaluates the synergistic effect of piperonyl butoxide on the formula I compounds of this invention. Piperonyl butoxide (PBO) is added in an amount of 1.5% to a 1,000 ppm solution of a test compound in acetone. Dilutions are then made with acetone to provide solutions containing 300, 100, 10 and 1 ppm of the test compound and 0.45%, 0.15%, 0.015% and 0.0015% piperonyl butoxide, respectively. Solutions containing 1,000, 300, 100, 10 and 1 ppm of the test compound alone are used as the control. The evaluations are conducted according to the procedure described in Example 1. The results are summarized in Table VII.

As can be seen from the data in Table VII, piperonyl butoxide significantly enhances the contact activity of the formula I compounds of this invention.

TABLE VII

Evaluation of Compositions Containing Test Compounds and Piperonyl Butoxide against *Ctenocephalides felis* (cat flea)

| Compound Number | Dose ($\mu g/cm^2$) | % PBO in Composition | 4 Hour % Mortality | 24 Hour % Mortality |
|---|---|---|---|---|
| 5 | 20.0 | 1.50 | 100 | 100 |
| | 6.2 | 0.45 | 20 | 100 |
| | 2.0 | 0.15 | 20 | 100 |
| | 0.2 | 0.015 | 40 | 100 |
| | 0.02 | 0.0015 | 0 | 70 |
| 5 | 20.0 | 0.0 | 100 | 100 |
| | 6.2 | 0.0 | 30 | 100 |

TABLE VII-continued

Evaluation of Compositions Containing Test Compounds and Piperonyl Butoxide against *Ctenocephalides felis* (cat flea)

| Compound Number | Dose ($\mu$g/cm$^2$) | % PBO in Composition | 4 Hour % Mortality | 24 Hour % Mortality |
|---|---|---|---|---|
| | 2.0 | 0.0 | 30 | 100 |
| | 0.2 | 0.0 | 20 | 20 |
| | 0.02 | 0.0 | 0 | 10 |

EXAMPLE 7

Evaluation of Test Compounds Against Ovine *Trichstrongylus colubriformis* Larvae This test is designed to evaluate the systemic activity of test compounds against helminth parasites. Mongolian gerbils are infected orally with ovine *Trichstrongylus colubriformis* larvae. Ten days post infection, the gerbils are treated with test compounds by diet incorporation. After feeding on the medicated diet for 3 days, the gerbils are sacrificed and gastrointestinal nematode populations are counted. Efficacy is determined by statistical analyses of treated versus non-treated nematode burdens. The results are summarized in Table VIII.

TABLE VIII

Evaluation of Test Compounds against Ovine *Trichstrongylus colubriformis* larvae

| Compound Number | Dose (ppm in feed) | % Efficacy |
|---|---|---|
| 5 | 500 | 46 |

EXAMPLE 8

Preparation of p-Chloro-α-methylhydratroponitrile

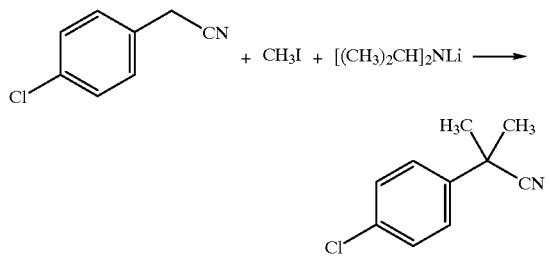

A solution of (p-chlorophenyl)acetonitrile (30.32 g, 0.20 mol) in tetrahydrofuran is treated dropwise with lithium diisopropylamide (0.44 mol, 220 mL of a 2 M solution in heptane/tetrahydrofuran/benzene) at −25° C. to −30° C. over 60 minutes under nitrogen, stirred at −15° C. for one hour, treated dropwise with a solution of iodomethane (62.45 g, 0.44 mol) in tetrahydrofuran at −15° C., stirred at −15° C. for one hour, and diluted with water. The aqueous solution is extracted with ether. The organic extract is washed sequentially with water, 2N hydrochloric acid and water, dried over anhydrous sodium sulfate, and concentrated in vacuo to obtain an oily residue. The residue is distilled to give the title product as a colorless oil (32.6 g, bp 89–91° C./1 mm Hg, 90.7% yield)

EXAMPLE 9

Preparation of 2-(p-Chlorophenyl)-2-methylpropionaldehyde

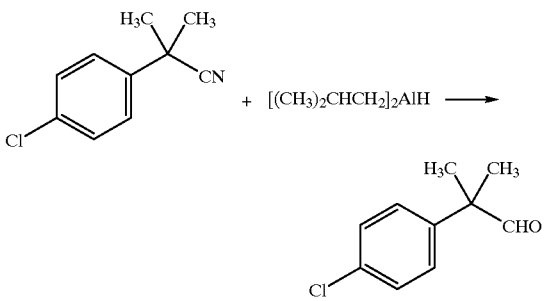

Diisobutylaluminum hydride (0.236 mol, 236 mL of a 1 M solution in hexane) is added over 90 minutes to a solution of p-chloro-α-methylhydratroponitrile (32.6 g, 0.181 mol) in diethyl ether under nitrogen at 0° C. After the addition is complete, water and 6 N hydrochloric acid are added to the reaction mixture while maintaining the temperature below 30° C. The resultant aqueous solution is stirred overnight at room temperature and extracted with diethyl ether. The organic extracts are combined, washed sequentially with 2 N hydrochloric acid and water, dried over anhydrous sodium sulfate, and concentrated in vacuo to give the title product as an oil (31.1 g, 94% yield).

Using essentially the same procedure, but substituting 1-(p-chlorophenyl)cyclopropanecarbonitrile for p-chloro-α-methylhydratroponitrile, 1-(p-chlorophenyl) cyclopropanecarboxaldehyde is obtained as a colorless solid, mp 38–41° C.

EXAMPLE 10

Preparation of 1,1-Dibromo-3-(p-chlorophenyl)-3-methyl-1-butene

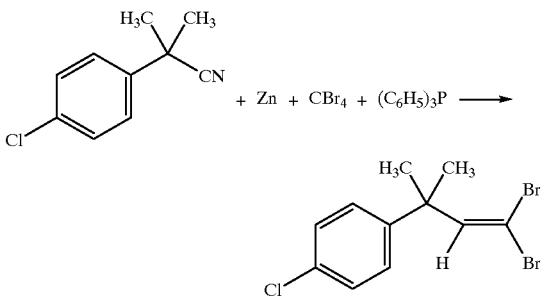

A solution of triphenyl phosphine (89.34 g, 0.34 mol) in methylene chloride is added dropwise to a mixture of zinc powder (22.27 g, 0.34 mol) and carbon tetrabromide (112.8 g, 0.34 mol) in methylene chloride at 20° C. over one hour. The resultant mixture is stirred at room temperature overnight, treated dropwise with a solution of 2-(p-chlorophenyl)-2-methylpropionaldehyde (31.1 g, 0.17 mol) in methylene chloride over 20 minutes, refluxed for 2 days, and poured into petroleum ether. The organic mixture is filtered through diatomaceous earth and concentrated in vacuo to obtain a residue. The residue is distilled to give the title product as an oil (38.5 g, bp 121–123° C./0.3 mm Hg, 66.8% yield).

Using essentially the same procedure, but substituting 1-(p-chlorophenyl)cyclopropanecarboxaldehyde for 2-(p-chlorophenyl-2-methylpropionaldehyde, 1-(2,2-dibromovinyl)-1-(p-chlorophenyl)cyclopropane is obtained as a colorless oil.

EXAMPLE 11

Preparation of 4-(p-Chlorophenyl)-4-methyl-2-pentynenitrile

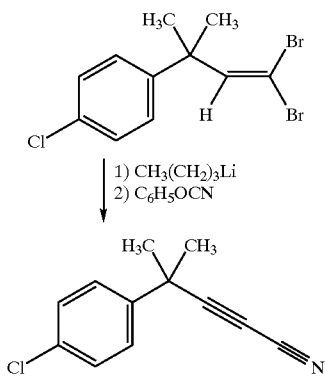

A solution of 1,1-dibromo-3-(p-chlorophenyl)-3-methyl-1-butene (38.5 g, 0.113 mol) in tetrahydrofuran is treated with n-butyllithium (0.25 mol, 100 mL of a 2.5 M solution in hexane) under nitrogen over 45 minutes while maintaining the temperature below −65° C., stirred overnight at dry ice/acetone bath temperature, treated dropwise with a solution of phenyl cyanate (14.89 g, 0.125 mol) in tetrahydrofuran over 30 minutes at −65° C. to −70° C., allowed to warm to 10° C., and diluted with ethyl acetate and 5% sodium hydroxide solution. The resultant mixture is extracted with ethyl acetate. The organic extracts are combined, washed sequentially with 5% sodium hydroxide solution and water, dried over anhydrous sodium sulfate and concentrated in vacuo to obtain a residue. The residue is distilled to give the title product as an oil (18.7 g, bp 110–113° C./0.9 mm Hg, 80.7% yield).

Using essentially the same procedure, but substituting 1-(2,2-dibromovinyl)-1-(p-chlorophenyl)cyclopropane for 1,1-dibromo-3-(p-chlorophenyl)-3-methyl-1-butene, 3-[1-(p-chlorophenyl)cyclopropyl]-2-propyne-1-carbonitrile is obtained as a yellow solid, mp 62–64° C.

EXAMPLE 12

Preparation of 4-(p-Chlorophenyl)-3-fluoro-4-methyl-2-pentenenitrile, (Z)—

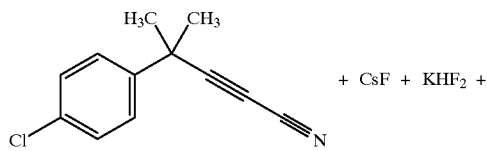

-continued

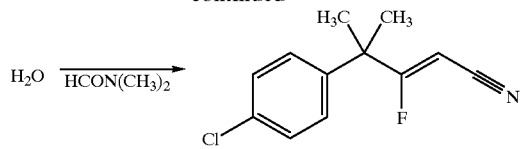

A mixture of cesium fluoride (41.38 g, 0.272 mol), potassium hydrogen fluoride (10.64 g, 0.136 mol) and water (13.07 g, 0.726 mol) in N,N-dimethylformamide is stirred for 10 minutes, treated with a solution of 4-(p-chlorophenyl)-4-methyl-2-pentynenitrile (18.5 g, 0.091 mol) in N,N-dimethylformamide, stirred at 80–85° C. for 4 hours, stirred at room temperature overnight and diluted with water. The aqueous mixture is extracted with ethyl acetate. The organic extracts are combined, washed with water, dried over anhydrous sodium sulfate and concentrated in vacuo to obtain a residue. Column chromatography of the residue using silica gel and a 1:9 ethyl acetate/hexane solution gives the title product as an oil (15.6 g, 76.8% yield).

Using essentially the same procedure, but substituting 3-[1-(p-chlorophenyl)cyclopropyl]-2-propyne-1-carbonitrile for 4-(p-chlorophenyl)-4-methyl-2-pentynenitrile, 1-(p-chlorophenyl)-β-fluorocyclopropaneacrylonitrile having a (Z)- to (E)- ratio of 9:1 is obtained as a colorless oil.

EXAMPLE 13

Preparation of 4-(p-Chlorophenyl)-4-methyl-2-pentenal, (Z)—

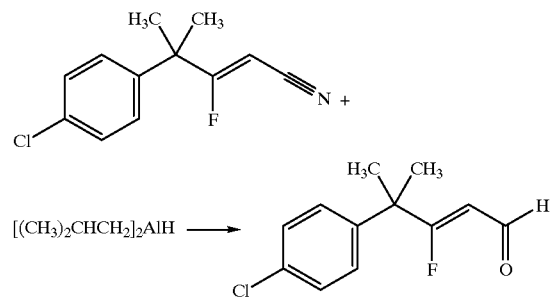

A solution of 4-(p-chlorophenyl)-3-fluoro-4-methyl-2-pentenenitrile, (Z)- (15.6 g, 69.7 mmol) in diethyl ether is treated dropwise with diisobutylaluminum hydride (83.6 mmol, 83.6 mL of a 1 M solution in hexane) over 90 minutes at −45° C. under nitrogen, stirred at −40° C. for 35 minutes, and diluted sequentially with water and 2 N hydrochloric acid at −10° C. The resultant aqueous mixture is stirred at room temperature for one hour and extracted with diethyl ether. The organic extracts are combined, washed sequentially with water, 2 N hydrochloric acid and water, dried over anhydrous sodium sulfate, and concentrated in vacuo to give the title product as a brown oil (15.34 g, 97% yield).

Using essentially the same procedure, but substituting 1-(p-chlorophenyl)-P-fluorocyclopropaneacrylonitrile having a (Z)- to (E)- ratio of 9:1 for 4-(p-chlorophenyl)-3-fluoro-4-methyl-2-pentenenitrile, (Z)-, 1-(p-chlorophenyl)-β-fluorocyclopropaneacrylaldehyde, (Z)- is obtained as a colorless oil.

EXAMPLE 14

Preparation of 4-(p-Chlorophenyl)-3-fluoro-4-methyl-2-penten-1-ol, (Z)—

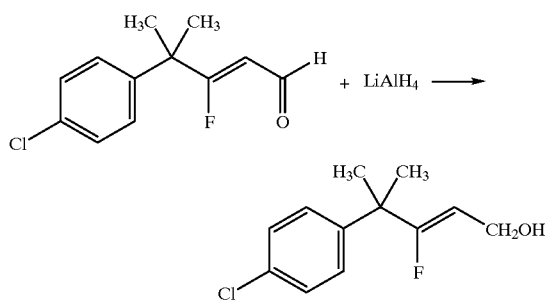

A solution of 4-(p-chlorophenyl)-4-methyl-2-pentenal, (Z)- (15.3 g, 67.5 mmol) in diethyl ether is added dropwise over 35 minutes to a mixture of lithium aluminum hydride (1.54 g, 40.5 mmol) in diethyl ether under nitrogen at −60° C. After the addition is complete, the reaction mixture is stirred for 20 minutes, and diluted sequentially with ethyl acetate, methanol and 2 N hydrochloric acid. The resultant mixture is stirred for 20 minutes and extracted with ethyl acetate. The combined organic extracts are washed sequentially with water and 2 N hydrochloric acid, dried over anhydrous sodium sulfate, and concentrated in vacuo to obtain a residue. Flash chromatography of the residue using silica gel and a 2:8 ethyl acetate/hexane solution gives the title product as an oil (10.6 g, 68.7% yield).

Using essentially the same procedure, but substituting 1-(p-chlorophenyl)-β-fluorocyclopropaneacrylaldehyde, (Z)- for 4-(p-chlorophenyl)-4-methyl-2-pentenal, (Z)-, 1-(p-chlorophenyl)-β-fluorocyclopropaneallyl alcohol, (Z)- is obtained as a colorless oil.

EXAMPLE 15

Preparation of 1-Bromo-4-(p-chlorophenyl)-3-fluoro-4-methyl-2-pentene, (Z)—

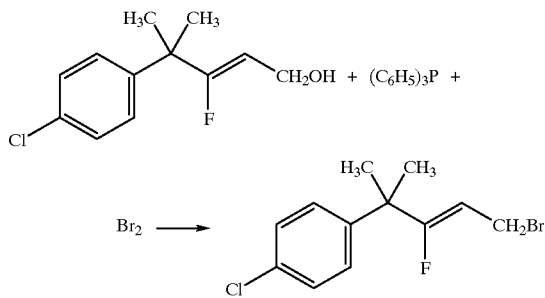

A solution of triphenyl phosphine (12.58 g, 55.6 mmol) in carbon tetrachloride at −5° C. to 5° C. is treated dropwise with a solution of bromine (8.89 g, 55.6 mmol) in carbon tetrachloride over 50 minutes under nitrogen, stirred at room temperature for one hour, treated with a solution of 4-(p-chlorophenyl)-3-fluoro-4-methyl-2-penten-1-ol, (Z)- (10.6 g, 46.3 mmol) in carbon tetrachloride over 15 minutes, refluxed for 2.5 hours, cooled to room temperature, and poured into petroleum ether. The resultant mixture is filtered through diatomaceous earth and concentrated in vacuo to obtain a residue. Flash chromatography of the residue using silica gel and a 1:9 ethyl acetate/hexane solution gives the title product as an oil (12.5 g, 92.6% yield).

Using essentially the same procedure, but substituting 1-(p-chlorophenyl)-β-fluorocyclopropaneallyl alcohol, (Z)- for 4-(p-chlorophenyl)-3-fluoro-4-methyl-2-penten-1-ol, (Z)-, 1-(p-chlorophenyl)-1-(3-bromo-1-fluoropropenyl) cyclopropane, (Z)- is obtained as a brown oil.

EXAMPLE 16

Preparation of 4-Fluoro-3-phenoxybenzeneboronic Acid

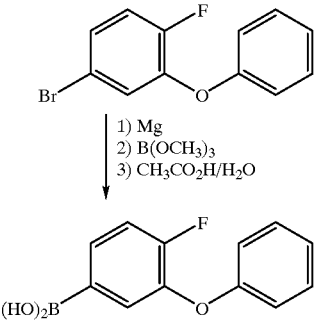

A solution of 5-bromo-2-fluorophenyl phenyl ether (8.01 g, 30 mmol) in tetrahydrofuran is added dropwise over 30 minutes to a mixture of magnesium turnings (0.0802 g, 33 mmol), a crystal of iodine and a few drops of 1,2-dibromoethane in tetrahydrofuran at 50–55° C. under nitrogen. After the addition is complete, the reaction mixture is stirred at 50–55° C. for 70 minutes and cooled to room temperature. The cooled mixture is added over 25 minutes to a solution of trimethyl borate (4.09 mL, 36 mmol) in diethyl ether at dry ice/acetone bath temperature. After the addition is complete, the mixture is stirred at dry ice/acetone bath temperature for 20 minutes, allowed to warm to −10° C. over 25 minutes, diluted sequentially with acetic acid and water, stirred at room temperature for 30 minutes, and extracted with ether. The organic extract is washed with water, dried over anhydrous sodium sulfate and concentrated in vacuo to obtain a residue. A mixture of the residue in water is heated over a steam bath for 30 minutes, cooled to room temperature and filtered to obtain a solid which is washed with hexanes and dried to give the title product as a colorless solid (5.7 g, mp 177–180° C., 82% yield).

Using essentially the same procedure, the following compounds are obtained:

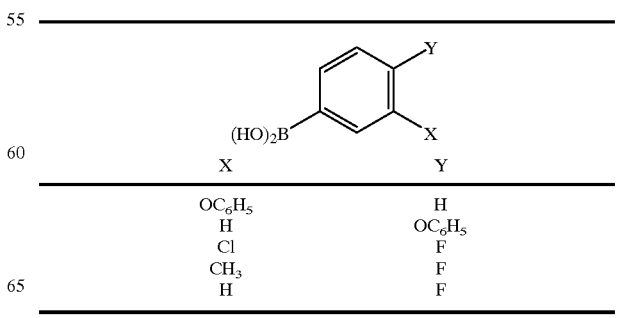

| X | Y |
|---|---|
| $OC_6H_5$ | H |
| H | $OC_6H_5$ |
| Cl | F |
| $CH_3$ | F |
| H | F |

EXAMPLE 17

Preparation of 4-(p-Chlorophenyl)-3-fluoro-1-(4-fluoro-3-phenoxyphenyl)-4-methyl-2-pentene, (Z)—

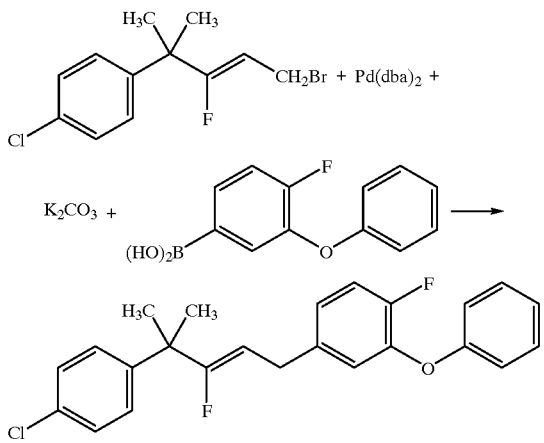

A mixture of 1-bromo-4-(p-chlorophenyl)-3-fluoro-4-methyl-2-pentene, (Z)- (1.02 g, 3.5 mmol), and bis(dibenzylideneacetone)palladium(0) [Pd(dba)$_2$] (0.1 g, 0.17 mmol) in toluene (20 mL) under nitrogen is stirred for one minute, treated with potassium carbonate (1.94 g, 0.014 mol), degassed, treated with a solution of 4-fluoro-3-phenoxybenzeneboronic acid (1.05 g, 4.55 mmol) in ethanol (5 mL), refluxed for 50 minutes, cooled to room temperature, diluted with ethyl acetate and filtered through diatomaceous earth. The filtrate is washed sequentially with water and brine, dried over anhydrous sodium sulfate and concentrated in vacuo to obtain a residue. Flash chromatography of the residue using silica gel and a 15:100 methylene chloride/hexane solution gives the title compound as a colorless oil (1.19 g, 85.6% yield) which is identified by NMR spectral analyses.

Using essentially the same procedure, the following compounds are obtained:

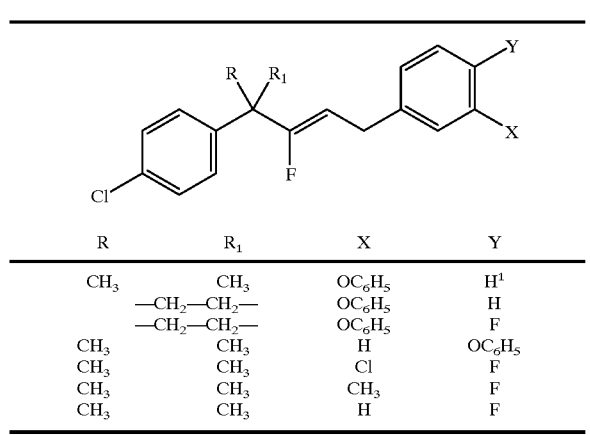

| R | R$_1$ | X | Y |
|---|---|---|---|
| CH$_3$ | CH$_3$ | OC$_6$H$_5$ | H[1] |
| —CH$_2$—CH$_2$— | | OC$_6$H$_5$ | H |
| —CH$_2$—CH$_2$— | | OC$_6$H$_5$ | F |
| CH$_3$ | CH$_3$ | H | OC$_6$H$_5$ |
| CH$_3$ | CH$_3$ | Cl | F |
| CH$_3$ | CH$_3$ | CH$_3$ | F |
| CH$_3$ | CH$_3$ | H | F |

[1] Z/E ratio 95:5

EXAMPLE 18

Preparation of Ethyl p-Chloro-β-cyclopropyl-α-fluorocinnamate, (E)- and (Z)—

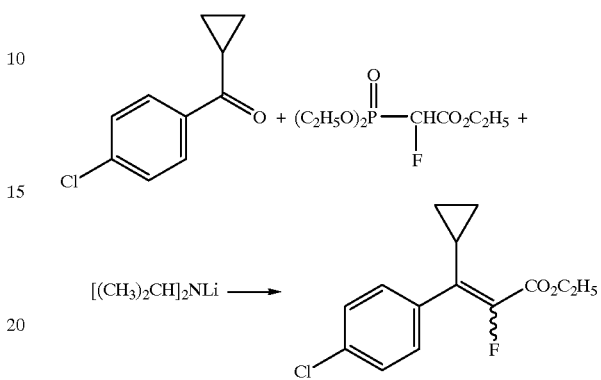

A solution of triethyl 2-fluoro-2-phosphonoacetate (49 g, 0.202 mol) in ether is cooled to −55 to −60° C., treated dropwise over 17 minutes with a 2.0 M solution of lithium diisopropylamide in heptane/tetrahydrofuran/ethylbenzene (116 mL, 0.232 mol), warmed to room temperature over 90 minutes, recooled to −55 to −60° C., treated over 10 minutes with a solution of 4-chlorophenyl cyclopropyl ketone (36.48 g, 0.202 mol) in ether, stirred at −55 to −60° C. for 20 minutes, warmed to and stirred at room temperature overnight, and quenched with water and 2 N hydrochloric acid (300 mL). The resultant aqueous mixture is extracted with ether. The organic extracts are combined, washed sequentially with water, 2 N hydrochloric acid and water, dried over anhydrous sodium sulfate, and concentrated in vacuo to obtain a residue. Kugelrohr distillation of the residue gives the title product as an oil (50 g, 92%, b.p. 100–110° C./0.5 mm Hg).

Using essentially the same procedure, the following compounds are obtained:

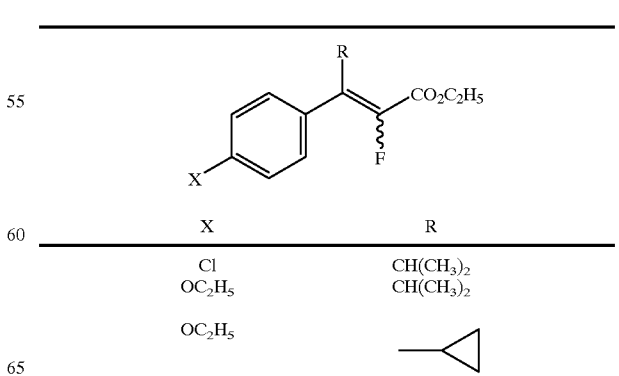

| X | R |
|---|---|
| Cl | CH(CH$_3$)$_2$ |
| OC$_2$H$_5$ | CH(CH$_3$)$_2$ |
| OC$_2$H$_5$ | ▷ |

EXAMPLE 19

Preparation of 3-(p-Chlorophenyl)-3-cyclopropyl-2-fluoro-2-propen-1-ol, (E)- and (Z)—

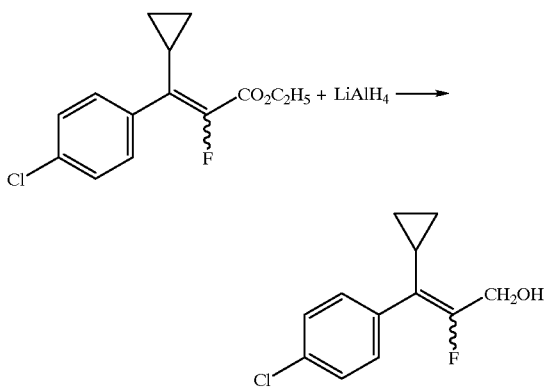

A solution of ethyl p-chloro-β-cyclopropyl-α-fluorocinnamate, (E)- and (Z)- (32.25 g, 0.12 mol) in ether is added dropwise to a mixture of lithium aluminum hydride (5.46 g, 0.144 mol) in ether while maintaining the temperature at −55° C. After the addition is complete, the reaction mixture is warmed to and stirred at −20° C. for 90 minutes, quenched sequentially with ethyl acetate, methanol and 2 N hydrochloric acid, and extracted with ether. The organic extracts are combined, washed sequentially with water, saturated sodium hydrogen carbonate solution and water, dried over anhydrous sodium sulfate, and concentrated in vacuo to give the title product as a colorless oil (26.4 g, 97%).

Using essentially the same procedure, the following compounds are obtained:

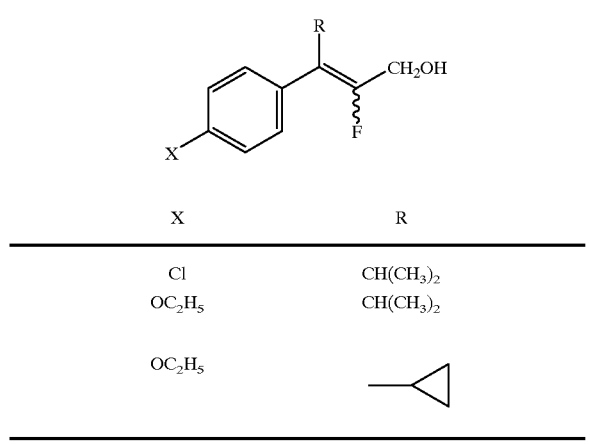

| X | R |
|---|---|
| Cl | CH(CH$_3$)$_2$ |
| OC$_2$H$_5$ | CH(CH$_3$)$_2$ |
| OC$_2$H$_5$ | ▷ |

EXAMPLE 20

Preparation of p-Chloro-β-cyclopropyl-α-fluorocinnamaldehyde

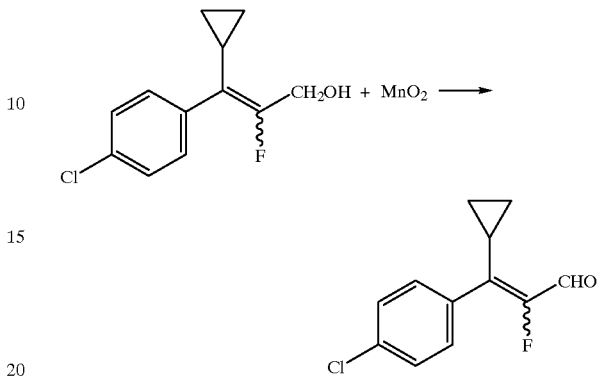

Activated manganese(IV) oxide (101.25 g, 1.16 mol) is added to a solution of 3-(p-chlorophenyl)-3-cyclopropyl-2-fluoro-2-propen-1-ol, (E)- and (Z)- (26.4 g, 0.116 mol) in hexanes. The resultant reaction mixture is stirred at room temperature overnight, filtered through a pad of diatomaceous earth, and concentrated in vacuo to obtain a residue. Flash column chromatography of the residue using silica gel and an ethyl acetate/hexanes solution (1:9) gives the title product as an oil (15.8 g, 60%).

Using essentially the same procedure, the following compounds are obtained:

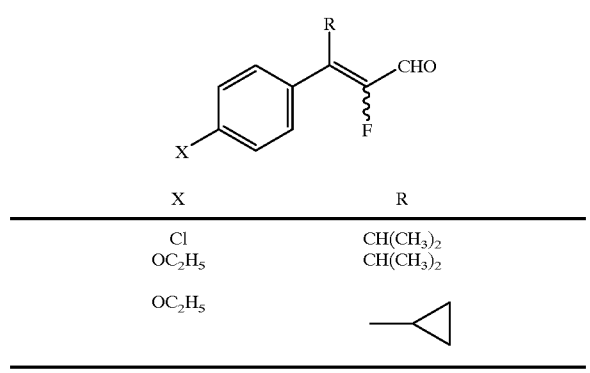

| X | R |
|---|---|
| Cl | CH(CH$_3$)$_2$ |
| OC$_2$H$_5$ | CH(CH$_3$)$_2$ |
| OC$_2$H$_5$ | ▷ |

EXAMPLE 21

Preparation of 1-[1-(p-Chlorophenyl)-2-methoxyvinyl]-cyclopropane, (E)- and (Z)—

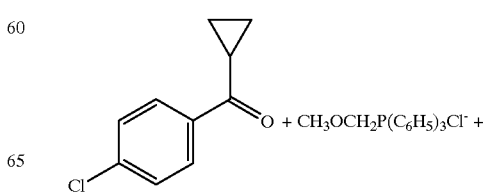

-continued

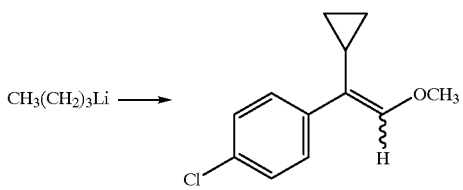

A solution of methoxymethyl triphenyl phosphonium chloride (20.5 g, 0.060 mol) in ether is cooled to −60° C., treated with a 2.5 M solution of butyllithium in hexanes (25.2 mL, 0.063 mol), warmed to and stirred at 0–5° C. for 90 minutes, recooled to −60° C., treated with a solution of 4-chlorophenyl cyclopropyl ketone (9.03 g, 0.050 mol) in ether, warmed to and stirred at room temperature overnight, quenched with ethyl acetate and 2 N hydrochloric acid, and extracted with ethyl acetate. The organic extracts are combined, washed sequentially with water, 2 N hydrochloric acid and water, dried over anhydrous sodium sulfate, and concentrated in vacuo to obtain a residue. Flash column chromatography of the residue using silica gel and an ethyl acetate/hexanes solution (1:9) gives the title product as an oil (6.2 g, 60%).

Using essentially the same procedure but substituting 4-fluorophenyl cyclopropyl ketone for 4-chlorophenyl cyclopropyl ketone, 1-[1-(p-fluorophenyl)-2-methoxyvinyl]-cyclopropane, (E)- and (Z)- is obtained as an oil.

EXAMPLE 22

Preparation of p-Chloro-β-cyclopropyl-α-fluorocinnamaldehyde

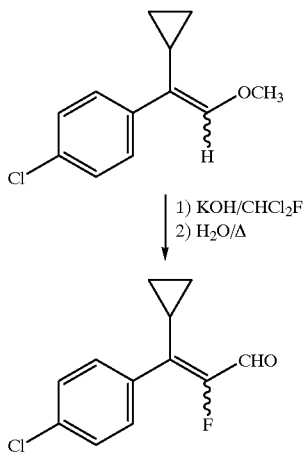

A mixture of potassium hydroxide (3.37 g, 0.060 mol), 18-Crown-6 (0.087 g, 0.33 mmol) and 1-[1-(p-chlorophenyl)-2-methoxyvinyl]cyclopropane, (E)- and (Z)- (3.13 g, 0.015 mol) in water is treated with dichlorofluoromethane (8 g, 0.077 mol) at 7–10° C., stirred at 10–13° C. overnight, treated with additional dichlorofluoromethane (6 g, 0.058 mol) at 7–10° C., stirred at 10–13° C. for 36 hours, treated with water, stirred at 70–75° C. for 4 hours, cooled to room temperature, and extracted with ethyl acetate. The organic extracts are combined, washed sequentially with water, 2 N hydrochloric acid and water, dried over anhydrous sodium sulfate, and concentrated in vacuo to obtain a residue. Flash column chromatography of the residue using silica gel and an ethyl acetate/hexanes solution (1:9) gives 1.02 g of the E-isomer of the title product and 0.69 g of the Z-isomer of the title product (1.71 g total product).

Using essentially the same procedure, but substituting 1-[1-(p-fluorophenyl)-2-methoxyvinyl]cyclopropane, (E)- and (Z)- for 1-[1-(p-chlorophenyl)-2-methoxyvinyl]-cyclopropane, (E)- and (Z)-, β-cyclopropyl-p,α-difluorocinnamaldehyde is obtained as an oil.

EXAMPLE 23

Preparation of (4-Fluoro-3-phenoxybenzyl)triphenyl Phosphonium Bromide

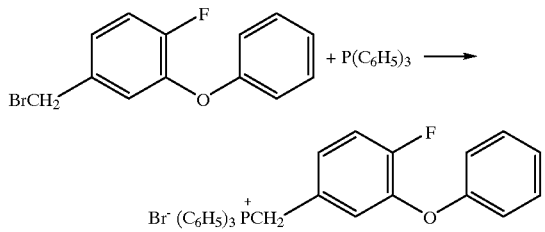

A solution of 4-fluoro-3-phenoxybenzyl bromide (42.17 g, 0.150 mol) in toluene is added to a solution of triphenyl phosphine (41.31 g, 0.158 mol) in toluene. The resultant reaction mixture is refluxed for one hour, cooled to room temperature, and filtered to obtain a solid. The solid is washed sequentially with toluene and hexanes, and dried in a dessicator at 60° C. to give the title product (73.7 g, 90.4%) which is identified by NMR spectral analyses.

Using essentially the same procedure, the following compounds are obtained:

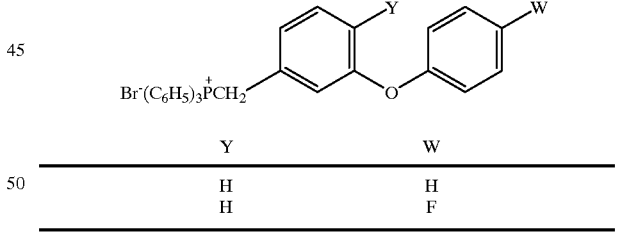

| Y | W |
|---|---|
| H | H |
| H | F |

EXAMPLE 24

Preparation of 1-(p-Chlorophenyl)-1-cyclopropyl-2-fluoro-4-(4-fluoro-3-phenoxyphenyl)-1,3-butadiene

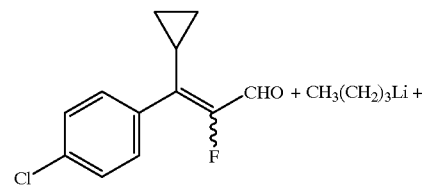

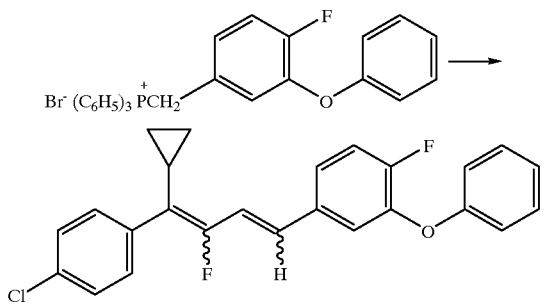

A mixture of (4-fluoro-3-phenoxybenzyl)triphenyl phosphonium bromide (41.77 g, 0.077 mol) in tetrahydrofuran is cooled to −55 to −60° C., treated dropwise with a 2.5 M solution of butyllithium in hexanes (32.15 mL, 0.080 mol), warmed to and stirred at room temperature for 2 hours, cooled to −55 to −60° C., treated dropwise with a solution of 2-fluoro-3-cyclopropyl-3-(p-chlorophenyl)acrylaldehyde (15.7 g, 0.070 mol) in tetrahydrofuran, warmed to and stirred at room temperature overnight, and quenched with ethyl acetate and 2 N hydrochloric acid. The resultant aqueous mixture is extracted with ethyl acetate. The organic extracts are combined, washed sequentially with water, 2 N hydrochloric acid and water, dried over anhydrous sodium sulfate, and concentrated in vacuo to obtain a residue. Flash column chromatography of the residue using silica gel and an ethyl acetate/hexanes solution (1:9) gives the title product as an oil (26.0 g, 91%).

Using essentially the same procedure, the following compounds are obtained:

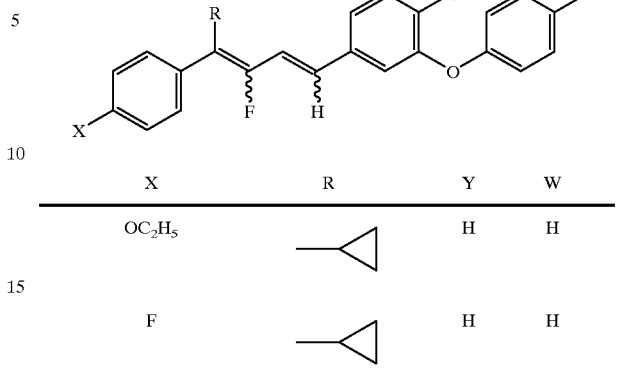

| X | R | Y | W |
|---|---|---|---|
| Cl | ▷ | H | H |
| Cl | CH(CH₃)₂ | F | H |
| Cl | CH(CH₃)₂ | H | H |
| OC₂H₅ | CH(CH₃)₂ | F | H |
| OC₂H₅ | ▷ | F | H |
| OC₂H₅ | CH(CH₃)₂ | H | H |
| OC₂H₅ | CH(CH₃)₂ | H | F |
| Cl | ▷ | H | F |
| F | ▷ | F | H |
| OC₂H₅ | ▷ | H | H |
| F | ▷ | H | H |

EXAMPLE 25

Preparation of 1-[1-(p-Chlorophenyl)-2-fluoro-4-(4-fluoro-3-phenoxyphenyl)-2-butenyl]cyclopropane, (R,S)-(Z)—

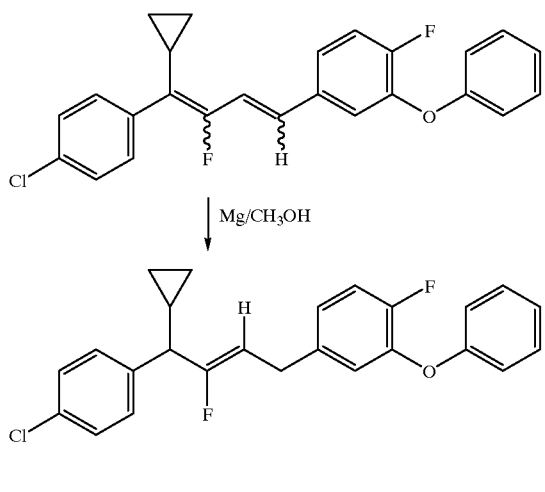

A solution of 1-(p-chlorophenyl)-1-cyclopropyl-2-fluoro-4-(4-fluoro-3-phenoxyphenyl)-1,3-butadiene (26 g, 0.064 mol) in a methanol/tetrahydrofuran solution (15:1) is treated with magnesium turnings (7.72 g, 0.317 mol), stirred at room temperature for 4 hours, quenched with hydrochloric acid, and extracted with ethyl acetate. The organic extracts are combined, washed sequentially with water, 2 N hydrochloric acid and water, dried over anhydrous sodium sulfate, and concentrated in vacuo to obtain a residue. Flash column chromatography of the residue using silica gel and an ethyl acetate/hexanes solution (5:95) gives the title product as an oil (21.4 g, 82%) which is identified by NMR spectral analyses.

Using essentially the same procedure, the following compounds are obtained:

| X | R | Y | W |
|---|---|---|---|
| Cl | cyclopropyl | H | H |
| Cl | CH(CH₃)₂ | F | H |
| Cl | CH(CH₃)₂ | H | H |
| OC₂H₅ | CH(CH₃)₂ | F | H |
| OC₂H₅ | cyclopropyl | F | H |
| OC₂H₅ | CH(CH₃)₂ | H | H |
| OC₂H₅ | CH(CH₃)₂ | H | F |
| Cl | cyclopropyl | H | F |
| F | cyclopropyl | F | H |
| OC₂H₅ | cyclopropyl | H | H |
| F | cyclopropyl | H | H |

EXAMPLE 26

Preparation of p-Chloro-α-isopropylbenzyl Alcohol

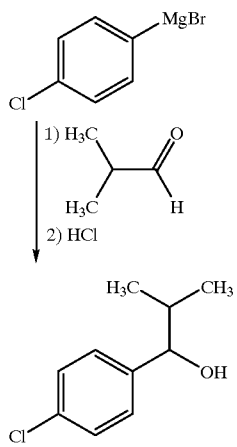

A 1 M solution of p-chlorophenylmagnesium bromide in diethyl ether (100 mL) is added to a solution of isobutyraldehyde (9.08 mL, 0.1 mol) in diethyl ether at −5° C. After the addition is complete, the reaction mixture is stirred overnight at room temperature, diluted with an ice-water mixture, and acidified with 10% hydrochloric acid. The phases are separated and the aqueous phase is extracted with diethyl ether. The organic phase and extracts are combined, washed sequentially with saturated sodium hydrogen carbonate solution, water and brine, dried over anhydrous sodium sulfate, and concentrated in vacuo to obtain an oil. Column chromatography of the oil using silica gel and a 33% methylene chloride in hexanes solution gives the title product as a colorless oil (14 g) which is identified by NMR spectral analyses.

Using essentially the same procedure, the following compounds are obtained:

| X |
|---|
| F |
| OCF₃ |

EXAMPLE 27

Preparation of 1-(1-Bromo-2-methylpropyl)-4-chlorobenzene

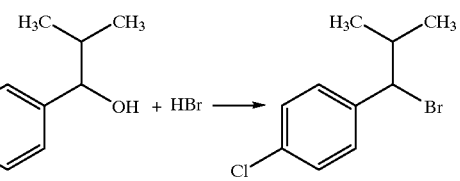

A mixture of p-chloro-α-isopropylbenzyl alcohol (33.08 g) in 48% hydrobromic acid (330 mL) is stirred at room temperature for 1 hour and extracted with hexanes. The combined organic extracts are washed sequentially with water, saturated sodium hydrogen carbonate solution and water, dried over anhydrous sodium sulfate, and concentrated in vacuo to give the title product as a yellow oil (42.98 g) which is identified by NMR spectral analysis.

Using essentially the same procedure, the following compounds are obtained:

| X |
|---|
| F |
| OCF₃ |

EXAMPLE 28

Preparation of 3-(p-Chlorophenyl)-1,1,2-trifluoro-4-methyl-1-pentene

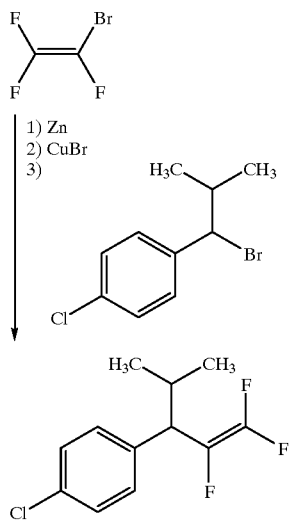

A mixture of zinc dust (15.72 g) and bromotrifluoroethylene (48.34 g, 0.30 mol) in N,N-dimethylformamide is heated to 38° C. After stirring at 38° C. for several minutes, the reaction mixture temperature rises to 65° C. over 30 minutes. The reaction mixture is then stirred for 90 minutes and cooled to −5° C. Copper(I) bromide (34.5 g, 0.24 mol) is then added to the cooled mixture. The reaction mixture is stirred at room temperature for 1 hour, treated sequentially with 1-(1-bromo-2-methylpropyl)-4-chlorobenzene (18.56 g, 0.075 mol) and limonene (5 drops), stirred at 49° C. overnight, cooled, and diluted with saturated ammonium chloride solution (400 mL) and concentrated ammonia solution (100 mL). The resultant aqueous mixture is extracted with hexanes. The combined organic extracts are washed sequentially with water, 10% hydrochloric acid, water, saturated sodium hydrogen carbonate solution and water, dried over anhydrous sodium sulfate, and concentrated in vacuo to obtain an oil. Column chromatography of the oil using silica gel and hexanes gives the title product as an oil (5.54 g) which is identified by NMR spectral analyses.

Using essentially the same procedure, the following compounds are obtained:

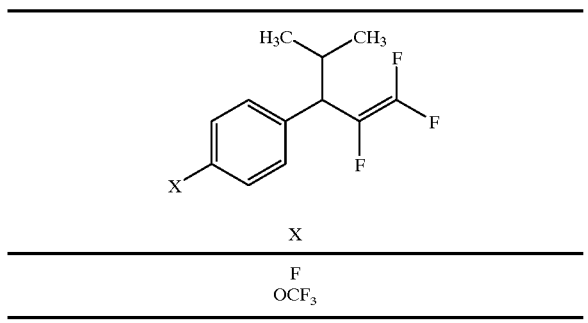

| X |
| --- |
| F |
| OCF₃ |

In addition, when 1-(p-ethoxyphenyl)-2-methylpropyl trifluoroacetate and 1-(p-methoxyphenyl)-2-methylpropyl trifluoroacetate are substituted for 1-(1-bromo-2-methylpropyl)-4-chlorobenzene, 3-(p-ethoxyphenyl)-1,1,2-trifluoro-4-methyl-1-pentene and 3-(p-methoxyphenyl)-1,1,2-trifluoro-4-methyl-1-pentene are obtained, respectively.

EXAMPLE 29

Preparation of 3-(p-Chlorophenyl)-1,2-difluoro-4-methyl-1-pentene

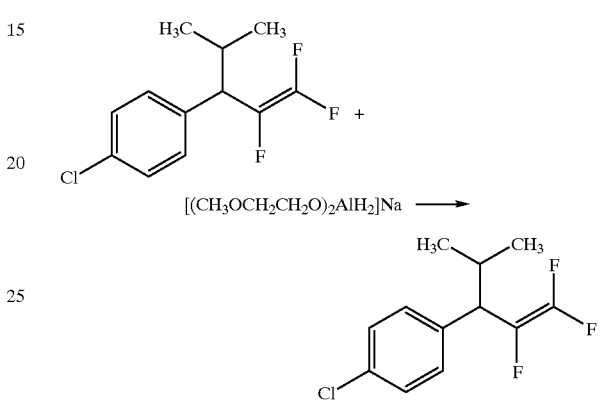

A solution of 3-(p-chlorophenyl)-1,1,2-trifluoro-4-methyl-1-pentene (2.48 g, 0.01 mol) in tetrahydrofuran is cooled to −8° C., treated dropwise with a 3.4 M solution of sodium bis(2-methoxyethoxy)aluminum hydride in toluene (3.1 mL), stirred overnight at room temperature, diluted with water, acidified with 10% hydrochloric acid, and extracted with methylene chloride. The combined organic extracts are washed sequentially with water, saturated sodium hydrogen carbonate solution and water, dried over anhydrous sodium sulfate, and concentrated in vacuo to obtain the title product as a yellow oil (2.10 g) which is identified by NMR spectral analyses.

Using essentially the same procedure, the following compounds are obtained:

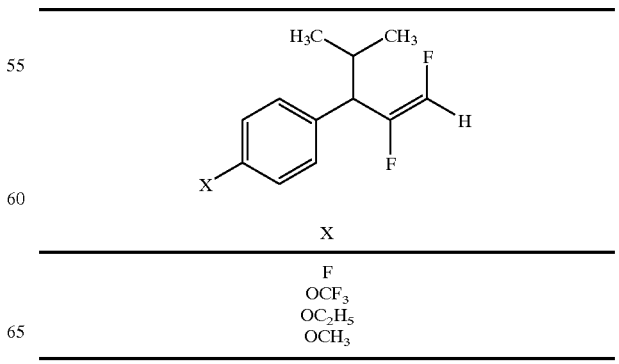

| X |
| --- |
| F |
| OCF₃ |
| OC₂H₅ |
| OCH₃ |

EXAMPLE 30

Preparation of 4-(p-Chlorophenyl)-2,3-difluoro-5-methyl-1-(m-phenoxyphenyl)-2-hexene, (E)—

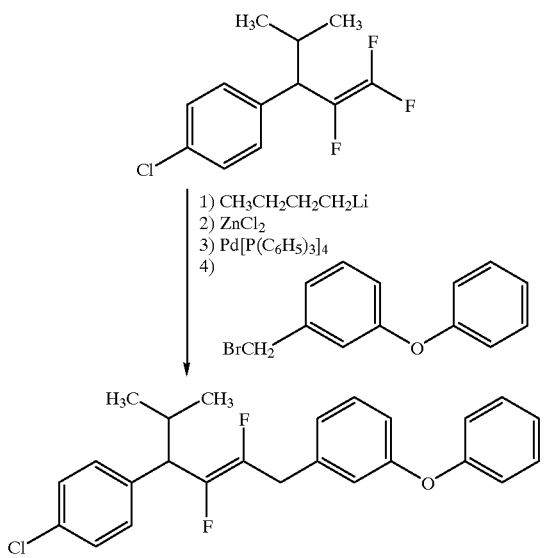

A solution of 3-(p-chlorophenyl)-1,2-difluoro-4-methyl-1-pentene (0.69 g, 0.003 mol) in tetrahydrofuran is cooled to −70° C., treated with a 2.5 M solution of n-butyllithium in hexane (1.2 mL), stirred at −60° C. for 1 hour, treated with a 0.5 M solution of zinc chloride in tetrahydrofuran (6 mL), stirred at −60° C. for 1 hour, treated sequentially with a solution of tetrakis(triphenylphosphine)palladium(0) (0.081 g) in tetrahydrofuran and a solution of α-bromo-m-tolyl phenyl ether (0.789 g, 0.003 mol) in tetrahydrofuran, stirred at room temperature overnight, diluted with water, acidified with 10% hydrochloric acid, and extracted with methylene chloride. The combined organic extracts are washed with water, dried over anhydrous sodium sulfate, and concentrated in vacuo to obtain an oil. Column chromatography of the oil using silica gel and pentane affords an oil which is purified by Kugelrohr distillation to give the title product as a pale, yellow oil (0.46 g) which is identified by NMR spectral analyses.

Using essentially the same procedure, the following compounds are obtained:

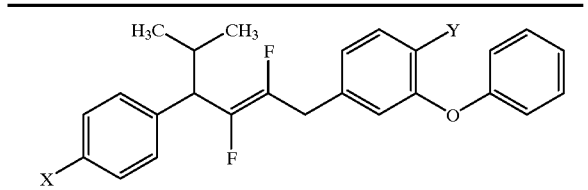

| X | Y | state |
|---|---|---|
| Cl | F | colorless oil |
| OCF₃ | H | pale, yellow oil |
| OCF₃ | F | yellow oil |
| F | H | yellow oil |
| F | F | yellow oil |
| OC₂H₅ | H | colorless oil |
| OC₂H₅ | F | pale, yellow oil |

-continued

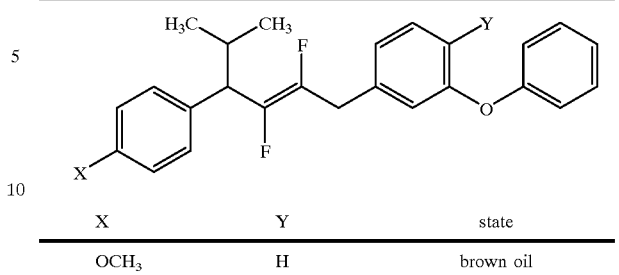

| X | Y | state |
|---|---|---|
| OCH₃ | H | brown oil |

EXAMPLE 31

Preparation of p-Ethoxy-α-isopropylbenzyl Alcohol

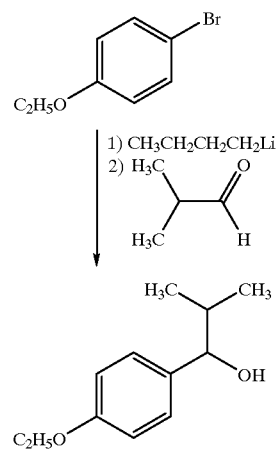

A solution of p-bromophenetole (2.01 g, 0.01 mol) in tetrahydrofuran is cooled to −65° C., treated dropwise with a 2.5 M solution of n-butyllithium in hexane (4 mL), stirred for 20 minutes at −55 to −65° C., treated dropwise with a solution of isobutyraldehyde (0.91 mL, 0.01 mol) in tetrahydrofuran, stirred overnight at room temperature, diluted with an ice-water mixture, acidified with 10% hydrochloric acid, and extracted with methylene chloride. The combined organic extracts are washed sequentially with water, saturated sodium hydrogen carbonate solution and water, dried over anhydrous sodium sulfate, and concentrated in vacuo to give the title product as a tan oil (1.95 g) which is identified by NMR spectral analyses.

Using essentially the same procedure, the following compound is obtained:

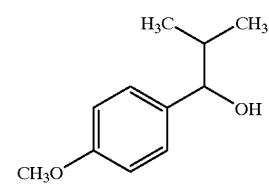

EXAMPLE 32

Preparation of 1-(p-Ethoxyphenyl)-2-methylpropyl Trifluoroacetate

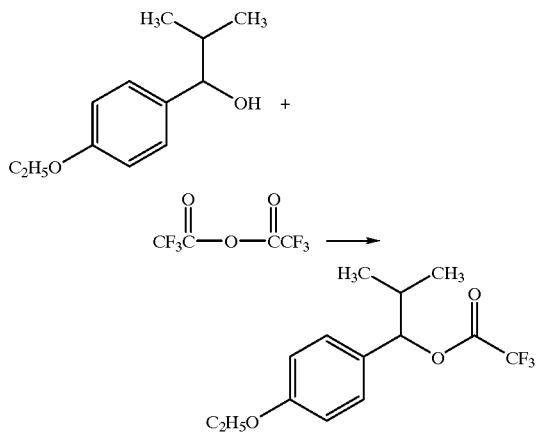

A mixture of trifluoroacetic anhydride (18 mL) in carbon tetrachloride is cooled with an ice-water bath, treated portionwise with a solution of p-ethoxy-α-isopropylbenzyl alcohol (9.0 g) in carbon tetrachloride, stirred at room temperature for 1 hour, concentrated in vacuo, diluted with carbon tetrachloride, and concentrated in vacuo to give the title product as a brown oil (13.23 g) which is identified by NMR spectral analysis.

Using essentially the same procedure, the following compound is obtained:

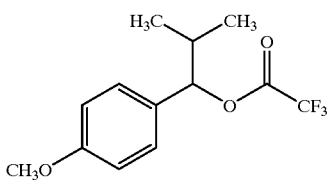

EXAMPLE 33

Preparation of p-[2,3-Difluoro-1-isopropyl-4-(m-phenoxyphenyl)-2-buten-1-yl]phenol, (E)—

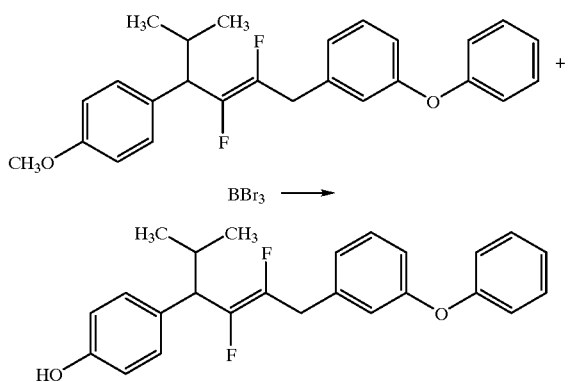

A solution of 2,3-difluoro-4-(p-methoxyphenyl)-5-methyl-1-(m-phenoxyphenyl-2-hexene, (E)- (0.408 g, 0.001 mol) in methylene chloride is cooled to −10° C., treated dropwise with a 1 M solution of boron tribromide in methylene chloride (1.0 mL, 0.001 mol), stirred overnight at room temperature, cooled, diluted with methanol, and concentrated in vacuo to obtain a residue. The residue is dissolved into methylene chloride. The resultant solution is washed sequentially with saturated sodium hydrogen carbonate solution and water, dried over anhydrous sodium sulfate, and concentrated in vacuo to obtain a brown oil. Column chromatography of the oil using silica gel and methylene chloride gives the title product as a pale, yellow oil (0.355 g) which is identified by NMR spectral analyses.

EXAMPLE 34

Preparation of 4-[p-(Difluoromethoxy)phenyl]-2,3-difluoro-5-methyl-1-(m-phenoxyphenyl)-2-hexene, (E)—

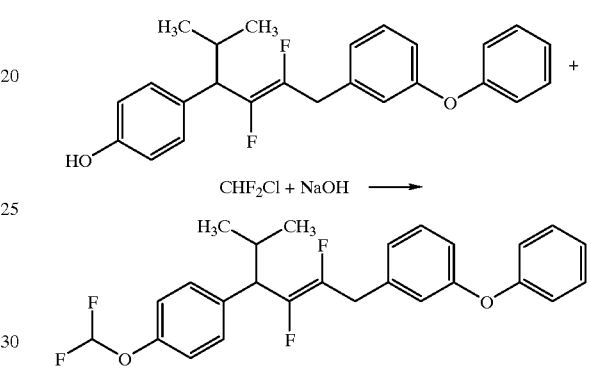

A mixture of p-[2,3-difluoro-1-isopropyl-4-(m-phenoxyphenyl)-2-buten-1-yl]phenol, (E)- (0.173 g), dioxane (6 mL) and water (4.5 mL) is treated sequentially with difluorochloromethane (70 drops) and sodium hydroxide (0.217 g), stirred at 70° C. for 1 hour, cooled, treated with additional difluorochloromethane (50 drops) and sodium hydroxide (0.245 g), heated at 58–66° C. for 3 hours, cooled, treated with additional difluorochloromethane (50 drops) and sodium hydroxide (0.185 g), heated for an additional 2.5 hours, stirred overnight at room temperature, and diluted with water. The resultant aqueous mixture is extracted with methylene chloride. The combined organic extracts are washed with water, dried over anhydrous sodium sulfate, and concentrated in vacuo to obtain a light brown oil. Column chromatography of the oil using silica gel and methylene chloride gives the title product as a colorless oil (0.134 g) which is identified by NMR spectral analyses.

What is claimed is:

1. A method of treatment for controlling, preventing and protecting animals and humans in need thereof from infestation and infection by arthropod or helminth parasites which comprises administering or applying to the animals, humans or their environment a parasiticidally effective amount of a compound having the structural formula

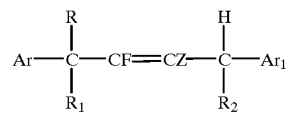

wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl, or R and $R_1$ taken together with the carbon atom to which they are attached form a $C_3$–$C_6$cycloalkyl ring optionally substituted with any combination of from one to three halogen or $C_1$–$C_4$alkyl groups, provided that when Z is F, $R_1$ is hydrogen;

Z is hydrogen or F;

$R_2$ is hydrogen, Cl, Br, cyano or $OR_3$;

$R_3$ is hydrogen or $C_1$–$C_4$alkyl; and $Ar_1$ is phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and the optical isomers thereof, and the (E)- and (Z)- isomers thereof.

2. The method according to claim 1 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl provided that at least one of R and $R_1$ is other than hydrogen, or R and $R_1$ taken together with the carbon atom to which they are attached form a $C_3$–$C_6$cycloalkyl ring optionally substituted with any combination of from one to three halogen or $C_1$–$C_4$alkyl groups, provided that when Z is F, $R_1$ is hydrogen;

Z is hydrogen or F;

$R_2$ is hydrogen, Cl, Br, cyano or $OR_3$;

$R_3$ is hydrogen or $C_1$–$C_4$alkyl; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

3. The method according to claim 2 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl and $R_1$ is hydrogen, or R and $R_1$ are methyl, or R and $R_1$ taken together with the carbon atom to which they are attached form a cyclopropyl ring, provided that when Z is F, $R_1$ is hydrogen;

Z is hydrogen or F;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

4. The method according to claim 3 wherein

Ar is phenyl optionally substituted with any combination of from one to three halogen, $C_1$––$C_4$alkyl, $C_1$–$C_4$haloalkyl, $C_1$–$C_4$alkoxy or $C_1$–$C_4$haloalkoxy groups;

R is isopropyl or cyclopropyl and $R_1$ is hydrogen, or R and $R_1$ are methyl, or R and $R_1$ taken together with the carbon atom to which they are attached form a cyclopropyl ring;

Z is hydrogen;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

5. The method according to claim 4 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl;

$R_1$ is hydrogen;

Z is hydrogen;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

6. The method according to claim 3 wherein the compound is selected from the group consisting of 4-(p-chlorophenyl)-3-fluoro-1-(4-fluoro-3-phenoxyphenyl)-4-methyl-2-pentene, (Z)-;
1-[1-(p-chlorophenyl)-2-fluoro-4-(4-fluoro-3-phenoxyphenyl)-2-butenyl]cyclopropane, (Z)-;
1-[1-(p-chlorophenyl)-2-fluoro-4-(m-phenoxyphenyl)-2-butenyl]cyclopropane, (Z)-;
4-(p-ethoxyphenyl)-3-fluoro-1-(4-fluoro-3-phenoxyphenyl)-5-methyl-2-hexene, (Z)-;
1-[1-(p-ethoxyphenyl)-2-fluoro-4-(4-fluoro-3-phenoxyphenyl)-2-butenyl]cyclopropane, (Z)-;
4-(p-ethoxyphenyl)-3-fluoro-5-methyl-1-(m-phenoxyphenyl)-2-hexene, (Z)-;
1-{1-(p-chlorophenyl)-2-fluoro-4-[m-(p-fluorophenoxy)phenyl]-2-butenyl}cyclopropane, (Z)-;
1-[1-(p-ethoxyphenyl)-2-fluoro-4-(m-phenoxyphenyl)-2-butenyl]cyclopropane, (R,S)-(Z)-;
1-[2-fluoro-1-(p-fluorophenyl)-4-(m-phenoxyphenyl)-2-butenyl]cyclopropane, (R,S)-(Z)-;
1-{1-(p-ethoxyphenyl)-2-fluoro-4-[4-fluoro-3-(p-fluorophenoxy)phenyl]-2-butenyl}cyclopropane, (R,S)-(Z)-;
2,3-difluoro-1-(4-fluoro-3-phenoxyphenyl)-5-methyl-4-[p-(trifluoromethoxy)phenyl]-2-hexene, (E)-; and
1-{[1-(p-chlorophenyl)-2-fluoro-4-[4-fluoro-3-(p-fluorophenoxy)phenyl]-2-butenyl]}cyclopropane, (R,S)-(Z)-.

7. The method according to claim 6 wherein the compound is

1-[1-(p-chlorophenyl)-2-fluoro-4-(4-fluoro-3-phenoxyphenyl)-2-butenyl]cyclopropane, (Z)-.

8. The method according to claim 1 which comprises topically applying a composition containing the compound to the skin, hide, fur, feathers or hair of the animals or humans.

9. The method according to claim 8 wherein the animals are selected from the group consisting of cattle, sheep, horses, deer, camels, swine, goats, ferrets, mink, rabbits, amphibians, reptiles, fish, birds, poultry, dogs and cats.

10. The method according to claim 8 wherein the composition is applied in solid, gel, paste or liquid form.

11. The method according to claim 8 for controlling and preventing infestation and infection by flies, fleas, lice, mosquitoes, gnats, mites and ticks.

12. The method according to claim 1 wherein the compound is orally, intragastrically or intrarumenally administered to the animals or humans.

13. The method according to claim 1 wherein the compound is parenterally administered to the animals or humans.

14. The method according to claim 1 wherein the animals are selected from the group consisting of cattle, sheep, horses, deer, camels, swine, goats, ferrets, mink, rabbits, amphibians, reptiles, fish, birds, poultry, dogs and cats.

15. The method according to claim 1 wherein the compound is administered or applied in combination with or in conjunction with one or more synergists.

16. The method according to claim 15 wherein the synergist is piperonyl butoxide.

17. The method according to claim 1 wherein the compound is administered or applied in combination with or in conjunction with one or more other parasiticidal compounds.

18. The method according to claim 1 wherein a composition containing the compound is applied to the animal's or human's environment.

19. The method according to claim 18 wherein the composition is applied as a spray, powder, bait, solid matrix, solution, wettable powder, emulsifiable concentrate or fumigant.

20. A composition for treating, controlling, preventing and protecting animals and humans from infestation and infection by arthropod or helminth parasites which composition comprises an agronomically or pharmaceutically acceptable carrier and a parasiticidally effective amount of a compound having the structural formula

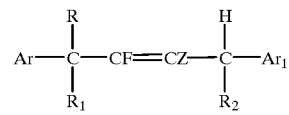

wherein
Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups,
1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or
a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;
R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl, or R and $R_1$ taken together with the carbon atom to which they are attached form a $C_3$–$C_6$cycloalkyl ring optionally substituted with any combination of from one to three halogen or $C_1$–$C_4$alkyl groups, provided that when Z is F, $R_1$ is hydrogen;
Z is hydrogen or F;
$R_2$ is hydrogen, Cl, Br, cyano or $OR_3$;
$R_3$ is hydrogen or C-$C_4$alkyl; and
$Ar_1$ is phenoxyphenyl optionally substituted with any combination of from one to six halogen, $C_1$–$C_4$alkyl, $C_3$–$C_4$haloalkyl, $C_1$–$C_4$alkoxy or $C_1$–$C_4$haloalkoxy groups,
phenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
phenoxypyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylpyridyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups,
benzoylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, 1- or 2-naphthyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, or a 5- or 6-membered heteroaromatic ring optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups, and the optical isomers thereof, and the (E)- and (Z)- isomers thereof.

21. The composition according to claim 20 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R and $R_1$ are each independently hydrogen, $C_1$–$C_4$alkyl, $C_1$–$C_4$haloalkyl, $C_3$–$C_6$cycloalkyl or $C_3$–$C_6$halocycloalkyl provided that at least one of R and $R_1$ is other than hydrogen, or R and $R_1$ taken together with the carbon atom to which they are attached form a $C_3$–$C_6$cycloalkyl ring optionally substituted with any combination of from one to three halogen or $C_1$–$C_4$alkyl groups, provided that when Z is F, $R_1$ is hydrogen;

Z is hydrogen or F;

$R_2$ is hydrogen, Cl, Br, cyano or $OR_3$;

$R_3$ is hydrogen or $C_1$–$C_4$alkyl; and $Ar_1$ is 3-phenoxyphenyl optionally substituted with any combination of from one to six halogen, $C_1$–$C_4$alkyl, $C_1$–$C_4$haloalkyl, $C_1$–C alkoxy or $C_1$–$C_4$haloalkoxy groups, 3-biphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups, or 3-benzylphenyl optionally substituted with any combination of from one to five halogen, $C_1$–$C_4$alkyl, $C_1$–$C_4$haloalkyl, $C_1$–$C_4$alkoxy or $C_1$–$C_4$haloalkoxy groups.

22. The composition according to claim 21 wherein

Ar is phenyl optionally substituted with any combination of from one to three halogen, $C_1$–$C_4$alkyl, $C_1$–$C_4$haloalkyl, $C_1$–$C_4$alkoxy or $C_1$–$C_4$haloalkoxy groups;

R is isopropyl or cyclopropyl and $R_1$ is hydrogen, or R and $R_1$ are methyl, or R and $R_1$ taken together with the carbon atom to which they are attached form a cyclopropyl ring, provided that when Z is F, $R_1$ is hydrogen;

Z is hydrogen or F;

$R_2$ is hydrogen; and $Ar_1$ is 3-phenoxyphenyl optionally substituted with any combination of from one to six halogen, $C_1$–$C_4$alkyl, $C_1$–$C_4$haloalkyl, $C_1$–$C_4$alkoxy or $C_1$–$C_4$haloalkoxy groups.

23. The composition according to claim 20 which further comprises one or more synergists.

24. The composition according to claim 23 wherein the synergist is selected from the group consisting of piperonyl butoxide, N-octyl bicycloheptene dicarboximide, dipropyl pyridine-2,5-dicarboxylate and 1,5a,6,9,9a,9b-hexahydro-4a (4H)-dibenzofurancarboxaldehyde.

25. The composition according to claim 20 which further comprises one or more other parasiticidal compounds.

* * * * *